United States Patent
Carniato et al.

(10) Patent No.: US 6,602,878 B1
(45) Date of Patent: Aug. 5, 2003

(54) ACYLQUANIDINE DERIVATIVES, METHOD FOR PREPARING SAME, APPLICATION AS MEDICINES AND PHARMACEUTICAL COMPOSITIONS CONTAINING THEM

(75) Inventors: Denis Carniato, Cagnes Sur Mer (FR); Thomas R. Gadek, Oakland, CA (US); Jean-Francois Gourvest, Claye-Souilly (FR); Jochen Knolle, Kriftel (DE); Anurschirwan Peyman, Kelkheim (DE); Jean-Marie Ruxer, Issy les Moulineaux (FR); Sarah C. Bodary, San Bruno, CA (US)

(73) Assignees: Aventis Pharma S.A. (FR); Genentech, Inc.

( * ) Notice: Subject to any disclaimer, the term of this patent is extended or adjusted under 35 U.S.C. 154(b) by 0 days.

(21) Appl. No.: 09/856,351
(22) PCT Filed: Nov. 23, 1999
(86) PCT No.: PCT/FR99/02878
§ 371 (c)(1), (2), (4) Date: Jun. 27, 2001
(87) PCT Pub. No.: WO00/31046
PCT Pub. Date: Jun. 2, 2000

(30) Foreign Application Priority Data

Nov. 24, 1998 (FR) .............................. 98 14781

(51) Int. Cl.$^7$ ............... C07D 239/16; C07C 279/22; A61K 31/505
(52) U.S. Cl. ............... 514/275; 514/563; 544/330; 544/332; 562/471
(58) Field of Search ............... 544/330, 332; 562/471; 514/275, 563

(56) References Cited

U.S. PATENT DOCUMENTS 6,005,117 A * 12/1999 Wehner et al. ........... 548/332.5

FOREIGN PATENT DOCUMENTS

| EP | 820988 | * | 1/1998 |
| EP | 0820991 |   | 1/1998 |
| WO | 9721726 |   | 6/1997 |

OTHER PUBLICATIONS

Derwent Abstract for EP 820988, 1998.*

* cited by examiner

Primary Examiner—Deepak Rao
(74) Attorney, Agent, or Firm—Muserlian, Lucas and Mercanti

(57) ABSTRACT

Acylquanidines of the formula

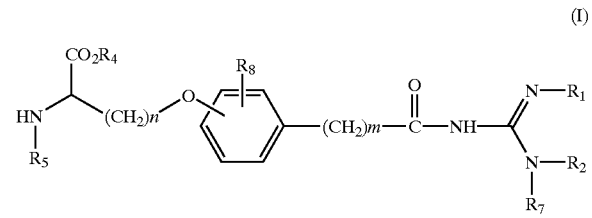

wherein the substituents are defined as in the specification which are antagonists of the vitronectin receptor and inhibitors of cell adhesion and bone resorption mediated by the osteoclasts.

15 Claims, No Drawings

ACYLGUANIDINE DERIVATIVES, METHOD FOR PREPARING SAME, APPLICATION AS MEDICINES AND PHARMACEUTICAL COMPOSITIONS CONTAINING THEM

This application is a 371 of PCT/FR99/02878 filed Nov. 23, 1999.

A subject of the present invention is new acylguanidine derivatives, their preparation process, their use as medicaments and the pharmaceutical compositions containing them.

A subject of the invention is the compounds of formula (I):

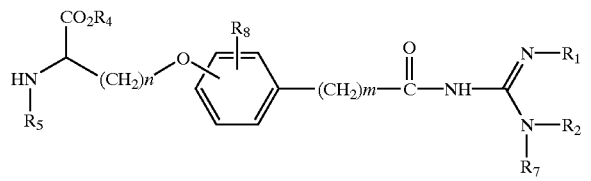

in which $R_1$, $R_2$, $R_4$, $R_5$, $R_7$ and $R_8$ have the meanings indicated below, their physiologically acceptable salts and their prodrugs. The compounds of formula (I) are compounds having a pharmacological activity and can therefore be used as medicaments. These are antagonists of the vitronectin receptor and inhibitors of cell adhesion and they inhibit bone resorption mediated by the osteoclasts. They are therefore useful for the therapeutic or prophylactic treatment of diseases which are caused at least in part by an undesirable increase in bone resorption, for example osteoporosis. A subject of the invention is also the preparation process for the compounds of formula (I), their use, in particular as medicaments and the pharmaceutical compositions containing them.

The bone is constantly subjected to a dynamic process which includes bone resorption and bone formation. These processes are mediated via specialized cells. Bone formation is the result of the deposit of a mineral matrix by the osteoblasts and bone resorption is the result of the dissolution of this bone matrix by the osteoclasts. The majority of bone disorders are caused by a disturbed equilibrium between bone formation and bone resorption. Osteoporosis is characterized by a dry loss of this bone matrix. An activated mature osteoclast resorbs the bone after adhesion to the bone matrix via the secretion of proteolytic enzyme, and protons inside the adhesion zone, resulting in depressions or hollows on the bone surface which appear when the osteoclast detaches itself from the bone.

Studies have shown that the fixation of the osteoclast on the bone is mediated by receptors: the integrins. Integrins are a superfamily of receptors mediating the cell/cell and more particularly cell/matrix adhesion process, including in particular $\alpha_{IIb}\beta_3$ as a blood platelet receptor (fibrinogen) and $\alpha_v\beta_3$ as vitronectin receptor. The peptides containing the RGD unit as well as the anti $\alpha_v\beta_3$ antibodies are known for their ability to inhibit resorbtion of dentin and prevention of osteoclast adhesion on the mineralized matrices (Horton et al. Exp. Cell. Res. (1991), 195, 368). The peptide Echistatine, isolated from snake venom also contains an RGD unit and is described as an inhibitor of the adhesion of osteoclasts to the bone and is a powerful inhibitor of bone resorption in tissues cultured in vitro (Sato et al. J. Cell. Biol. (1990), 111, 1713) and in vivo in the rat (Fisher et al. Endocrinology (1993), 132, 1411).

The $\alpha_v\beta$ receptor is a transmembrane glycoprotein which is expressed in a large number of cells including endothelial cells, smooth muscle cells, osteoclast and cancerous cells which thus leads to a pluripotentiality of the compounds of formula (I) according to the invention.

In fact, the $\alpha_v\beta$ receptors expressed in the membrane of the osteoclasts are the basis of the adhesion/resorption process, contribute to the organization of the cell cytoskeleton, and are involved in osteoporosis. The $\alpha_v\beta$ receptors expressed in the smooth muscle cells of the aorta, stimulate their migration towards the neointima, which leads to the formation of arteriosclerosis and the occurrence of post-angioplastic recurrence of stenosis (Brown et al., cardiovascular Res. (1994), 28, 1815). The endothelial cells secrete growth factors which are mitogens for the endothelium and can contribute to the formation of new blood vessels (Angiogenesis).

The antagonists of $\alpha_v\beta$ integrin can therefore lead to a regression of cancerous tumors by inducing apoptosis of the angiogenic blood vessels. (Brook et al. Cell (1994) 79, 1157).

Cheresh et al (Science 1995, 270, 1500) have described anti-$\alpha_v\beta$ antibodies or antagonists of the $\alpha_v\beta$ receptor which inhibit the process of angiogenesis induced by bFGF in the rat eye, a property which can be used for the treatment of retinopathies, in particular in diabetics.

The patent application WO-A-94/12181 describes aromatic or non-aromatic substituted systems and WO-A-94/08577 describes substituted heterocycles as antagonists of the fibrinogen receptor and inhibitors of platelet aggregation. EP-A-528586 and EP-A-528587 describe phenylalanine derivatives substituted by an aminoalkyl or a heterocycle and WO-A-95/32710 describes aryl derivatives as inhibitors of bone resorption by the osteoclasts. WO-A-96/00574 describes benzodiazepines and WO-A-96/00730 describes compounds which inhibit the fibrinogen receptor, in particular benzodiazepines which are linked to a ring with 5 nitrogenous members as antagonists of the vitronectin receptor. DE-A-19654483 describes tyrosine derived antagonists of the vitronectin receptor. DE-A-19629816.4 claims cycloalkyl derivatives as antagonists of the vitronectin receptor. Other investigations have made it possible to show that the acylguanidine derivatives of formula (I) show marked activity as inhibitors of the vitronectin receptor and of bone resorption mediated via the osteoclasts.

A subject of the invention is the compounds of formula (I)

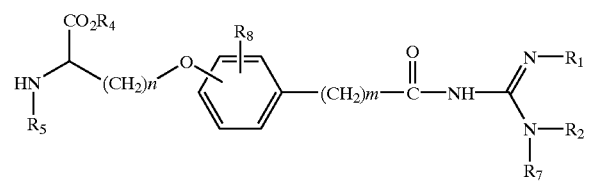

in which
either $R_1$ and $R_2$, independently from one another represent a hydrogen atom or an alkyl group containing 1 to 6 carbon atoms non-substituted or substituted by $R_3$, or $R_1$ and $R_2$ together form a divalent alkylene radical containing 2 to 9 carbon atoms, saturated or unsaturated, such as $-(CH_2)_p-$ in which p is 2, 3, 4, 5, 6, 7, 8 or 9, non-substituted or substituted by one or more radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl, $(C_3-C_{12})$-cycloalkyl-$(C_1-C_6)$-alkyl and oxo, the said divalent alkylene radical being able to be attached at the level of the carbon-carbon bond to a carbocycle or a heterocycle with 5 to 7 members, containing 1 or 2 nitrogen atoms, saturated or unsaturated, non-substituted or substituted by 1 or 2 $R_3$ radicals;

$R_3$ represents a $(C_1-C_8)$-alkyl, $(C_1-C_8)$-alkoxy, $(C_5-C_{14})$-aryl, $(C_5-C_{14})$-aryl-$(C_1-C_4)$-alkyl, halogen, trifluoromethyl, hydroxyl, nitro, amino, NH—$((C_1-C_4)$-alkyl$)$,N$((C_1-C_4)$alkyl$)_2$, NHCO—$(C_1-C_4)$-alkyl or CO—$(C_1-C_4)$alkyl group;

$R_4$ represents
  either a hydrogen atom,
  or a $(C_1-C_6)$-alkyl-CO—O—$(C_1-C_4)$-alkyl or $(C_1-C_6)$-alkyl group, non-substituted or substituted by a radical chosen from hydroxyl, $(C_1-C_4)$-alkoxy, $(C_1-C_4)$-alkyl-$SO_2$, $NR_9R_9'$ and $N^+R_9R_9'R_9''Q^-$, in which $R_9$, $R_9'$ and $R_9''$ independently from one another, represent a hydrogen, a $(C_1-C_6)$-alkyl, $(C_5-C_{14})$-aryl or $(C_5-C_{14})$-aryl-$(C_1-C_6)$-alkyl group and $Q^-$ is a physiologically acceptable anion,
  or one of the following radicals:

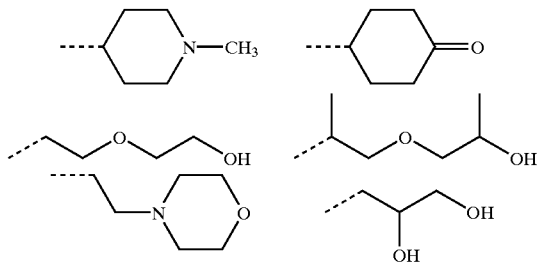

the dotted lines representing the position of the bond;

$R_5$ represents a hydrogen atom or a group chosen from $COR_6$, $CO_2R_6$, $SO_2R_6$, $SO_2NHR_6$, $SO_2NHCOR_6$, $SO_2NHCO_2R_6$,$CONH_2$ and $CONHR_6$ in which $R_6$ represents $(C_1-C_8)$-alkyl, $(C_6-C_{14})$-aryl, $(C_6-C_{14})$-aryl-$(C_1-C_6)$-alkyl, $(C_5-C_{14})$-heteroaryl or $(C_5-C_{14})$-heteroaryl-$(C_1-C_6)$-alkyl, $(C_3-C_{20})$ (mono-, bi- or tri-)-cycloalkyl, $(C_3-C_{20})$ (mono-, bi- or tri-)-cycloalkyl-$(C_1-C_6)$alkyl, the aryl, heteroaryl, alkyl or cycloalkyl radicals being non-substituted or substituted by 1, 2 or 3 $R_3$ radicals;

$R_7$ represents a hydrogen atom, $(C_1-C_6)$-alkyl-O—CO—, hydroxyl, $(C_1-C_6)$-alkyl-O—CO—O or nitro;

$R_8$ represents a hydrogen atom, halogen atom or an alkyloxy radical containing 1 to 6 carbon atoms;

m is equal to 0, 1, 2 or 3;

n is an integer equal to 1, 2 or 3;

the said compounds of formula (I) being in all their possible isomer forms, alone or in a mixture of any ratio, the acylguanidine group adjacent to the phenyl in para or meta position of the oxygen, as well as their physiologically acceptable salts and their promedicaments (prodrugs).

All the radicals which can be found several times in the compounds of formula (I), for example the $R_3$ radical, are independant from one another and can be identical or different.

The alkyl radicals can be linear or branched, saturated or mono- or polyunsaturated. This also applies when they carry a substituent or when they are included in groups such as for example alkoxy, alkoxycarbonyl, aralkyl or heteroarylalkyl groups.

By $(C_1-C_8)$-alkyl is meant the methyl, ethyl, propyl, butyl, pentyl, hexyl, heptyl, octyl, nonyl radicals; the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Among the preferred radicals methyl, ethyl, n-propyl, isopropyl, n-butyl, isobutyl, and tert-butyl can be mentioned.

The divalent alkylene radicals corresponding to the monovalent radicals mentioned above are for example the methylene, ethylene, 1,3-propylene, 1,2-propylene (=1-methylethylene), 2,3-butylene (=1,2-dimethylethylene), 1,4-butylene, or 1,6-hexylene radicals.

The unsaturated alkyl radicals are for example the alkenyl radicals such as vinyl, 1-propenyl, allyl, butenyl, 3-methyl-2-butenyl or the alkynyl radicals such as ethynyl, 1-propynyl or propargyl.

By unsaturated divalent alkylene radicals is meant the alkenylene and alkynylene radicals which can also be linear or branched. They are for example vinylene, propenylene, ethynylene or propynylene radicals.

The cycloalkyl radicals can be monocyclic, bicyclic or tricyclic. They are for example cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl radicals which can if appropriate be substituted for example by an alkyl containing 1 to 4 carbon atoms. As substituted cycloalkyl radicals, 4 methylcyclo-hexyl and 2,3-dimethylecyclo-hexyl can be mentioned.

The bicycloalkyl and tricycloalkyl radicals can be non-substituted or substituted in any position, for example by one or more oxo groups and/or 1 or more identical or different alkyl groups such as methyl or isopropyl and preferably methyl alkyl groups. The junction bond of the bi or tricyclic radical can be situated in all positions of the molecule. The bond can be situated at the bridged carbon atom or one of the other carbon atoms. This bond can also take any position from the point of view of the stereochemistry, for example exo or endo. As an example of bicycloalkyl or tricycloalkyl radicals, camphanyl, bornyl, adamantyl such as 1-adamantyl or 2-adamantyl, caranyl, epiisobornyl, epibornyl, norbornyl or norpinanyl can be mentioned.

By halogen is meant fluorine, chlorine, bromine or iodine.

By the term $(C_5-C_{14})$-aryl is meant
  either the $(C_5-C_{14})$-aryl heterocyclic radicals (=$(C_5-C_{14})$-heteroaryl), in which the carbon atoms of the ring are replaced by a heteroatom such as nitrogen, oxygen or sulphur,
  or the carbocyclic $(C_6-C_{14})$-aryl radicals.

Among the carbocyclic $(C_6-C_{14})$-aryl radicals, phenyl, naphthyl, biphenylyl, anthryl or fluorenyl and more particularly 1-naphthyl, 2-naphthyl and phenyl can be mentioned.

Unless indicated to the contrary, the aryl radicals, in particular phenyl, can be non-substituted or substituted by one or more identical or different radicals chosen from $(C_1-C_8)$-alkyl, in particular $(C_1-C_4)$alkyl, $(C_1-C_8)$-alkoxy, halogen such as fluorine, chlorine and bromine, nitro, amino, trifluoromethyl, hydroxyl, methylenedioxy, cyano, hydroxycarbonyl, aminocarbonyl, $(C_1-C_4)$-alkoxycarbonyl, phenyl, phenoxy, benzyl and benzyloxy. In general, 2 nitro groups at the most can be used in the compounds of formula (I) according to the invention.

In the case of monosubstituted phenyl, the substituent can be situated in position 2, 3 or 4, and preferably in position 3 or 4. In the case where the phenyl is di-substituted, the substituents can be in position 2, 3 or 2, 4 or 2, 5 or 2, 6 or 3, 4 or 3, 5. Preferably, in the di-substituted phenyls, the two substituents are in position 3, 4. When this phenyl is tri-substituted the positions are the following: 2, 3, 4 or 2, 3, 5 or 2, 3, 6 or 2, 4, 5 or 2, 4, 6 or 3, 4, 5. In the same way, the naphthyl radicals or other aryl radicals can be substituted in any position, for example the 1-naphthyl radical in position 2-, 3-, 4-, 5-, 6-, 7-, and 8 and the 2-naphthyl radical in position 1-, 3-, 4-, 5-, 6-, and 7.

The ($C_5$–$C_{14}$)-aryl group can also represent a monocyclic or polycyclic aromatic system in which 1, 2, 3, 4 or 5 carbon atoms of the ring are replaced by heteroatoms, in particular, identical to or different from the group constituted by nitrogen, oxygen and sulphur. Among the heterocyclic ($C_5$–$C_{14}$)-aryls (=($C_5$–$C_{14}$)-heteroaryl) groups there can be mentioned the 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups, or also benzo-condensed, cyclopenta-, cyclohexa-, or cyclohepta-condensed derivatives of these radicals. The heterocyclic system can be substituted by the same substituents mentioned above for the carbocyclic system.

Among the heteroaryl radicals, monocyclic or bicyclic aromatic systems having 1, 2 or 3 heteroatoms, in particular 1 or 2 heteroatoms are preferred, chosen from N, O or S, and which are non-substituted or substituted by groups such as ($C_1$–$C_6$)-alkyl, ($C_1$–$C_6$)-alkoxy, fluorine, chlorine, nitro, amino, trifluoromethyl, hydroxyl, ($C_1$–$C_4$)-alkoxycarbonyl, phenyl, phenoxy, benzyloxy, and benzyl.

Quite particularly, the monocyclic or bicyclic aromatic systems containing 5 to 10 members having 1 to 3 heteroatoms, in particular 1 or 2 heteroatoms, chosen from N, O and S and which can be substituted by 1 or 2 substituents such as ($C_1$–$C_4$)-alkyl, ($C_1$–$C_4$)-alkoxy, phenyl, phenoxy, benzyl and benzyloxy can be mentioned.

When $R_1$ and $R_2$ together form a divalent alkylene radical containing 2 to 9 carbon atoms, $R_1$ and $R_2$ form together with the two nitrogen atoms to which they are linked and the central carbon atom of the guanidine to which the two nitrogen atoms are linked, a 1,3-diazaheterocycle which is linked to the nitrogen atom in the $(CH_2)_m$—CO—NH group via its position 2.

As an example of 1,3-diazaheterocycles which can be substituted as indicated at the level of the ($C_2$–$C_9$)-alkylene radical or the nitrogen atom of the guanidine, there can be mentioned the 2-imidazolyl radical, the 4,5-dihydro-2-imidazolyl radical, the 1,4,5,6-tetrahydro-2-pyrimidinyl radical or the 4,5,6,7-tetrahydro-1H-1,3-diazepin-2-yl radical.

In the case where a ring of 5 to 7 members is condensed at the level of the carbon-carbon bond of the ($C_2$–$C_9$)-alkylene radical, then $R_1$ and $R_2$ form together with the two nitrogen atoms to which they are linked and the central carbon atom of the guanidine to which the two nitrogen atoms are linked, a bicyclic heterocycle which is linked to the nitrogen atom of the $(CH_2)_m$—CO—NH group and which can be substituted as indicated above.

The rings with 5 to 7 members condensed at the level of the carbon-carbon bond of the ($C_2$–$C_9$)-alkylene radical can be saturated, mono-unsaturated, di-unsaturated or aromatic; they can for example be cyclopropane, cyclohexane, cyclohexene, cyclohexadiene, cycloheptane or benzene.

Among the bicyclic aromatic systems linked to the nitrogen atom of the $(CH_2)_m$—CO—NH group, the 1,3a,4,5,6,6a-hexahydro-1,3-diazapentalen-2-yl radical, the 1H-2-benzimidazolyl radical, the 3a,4,5,6,7,7a-hexahydro-1H-benzymidazol-2-yl radical, the 4,5,6,7-tetrahydro-1H-benzimidazol-2-yl radical, the 4,7-dihydro-1H-benzimidazole-2-yl radical or the 1H-imidazo[4,5-b]pyridin-2-yl radical can be mentioned.

In the case where the condensed ring is substituted and/or the ($C_2$–$C_9$)-alkylene radical is substituted, they are preferably mono- or di-substituted independently from one another by an identical or different $R_3$ radical.

In the case where $R_1$ and/or $R_2$ are substituted alkyl groups, they are preferably mono- or di-substituted independently from one another by an identical or different $R_3$ radical.

The optically active carbon atoms contained in the compounds of formula (I) can independently from one another show the R configuration or the S configuration.

The compounds of formula (I) can be in the form of pure enantiomers or of pure diastereoisomers or in the form of a mixture of enantiomers, for example in the form of racemates or diastereoisomer mixtures.

A subject of the present invention is therefore pure enantiomers, mixtures of these enantiomers, pure diastereoisomers and mixtures of these diastereoisomers.

The invention relates to the mixtures of two or more than two stereoisomers of formula (I) and all the ratios of these stereoisomers in the said mixtures.

The compounds of formula (I) can, if appropriate, be present in the form of E or Z isomers. A subject of the invention is therefore pure E isomers, pure Z isomers and E/Z mixtures in any ratio.

The invention also relates to all the tautomer forms of the compounds of formula (I), relating for example to the form represented by formula (I), the form in which acylguanidine is present in the form of a —CO—N=C($NHR_1$)—$NR_2R_7$ group and all the other forms which differ by the different position of the hydrogen atom are considered.

Finally, the invention relates to the different regioisomers linked to the para or meta position of the oxygen atom adjacent to the phenyl. They therefore include the following isomers: oxygen in position 4 and $R_8$ in position 3, oxygen in position 4 and $R_8$ in position 2, oxygen in position 3 and $R_8$ in position 4, oxygen in position 3 and $R_8$ in position 2, oxygen in position 3 and $R_8$ in position 5, oxygen in position 3 and $R_8$ in position 6. Preferably the oxygen is in position 4 and $R_8$ is in position 3.

The diastereoisomers, including the E/Z isomers can be separated into individual isomers, for example by chromatography. The racemates can be separated into two enantiomers by current methods such as chiral phase chromatography or by resolution methods.

The physiologically acceptable salts of the compounds of formula (I) are in particular salts which can be used pharmaceutically or non-toxic salts, or salts which can be used physiologically.

When the compounds of formula (I) contain an acid group such as carboxylic acid, they are for example salts of alkali or alkaline-earth metals such as sodium, potassium, magnesium, calcium salts, and also the salts formed with physiologically acceptable quaternary ammonium ions and the addition salts with acids such as ammonia and physiologically acceptable organic amines such as for example triethylamine, ethanolamine or tris-(2-hydroxyethyl)amine.

When the compounds of formula (I) contain a basic group, they can form an addition salt with acids for example with inorganic acids such as hydrochloric, sulphuric, phosphoric acid or with organic carboxylic acids such as acetic, trifluoroacetic, citric, benzoic, maleic, fumaric, tartaric, methanesulphonic or para toluene sulphonic acid.

The compounds of formula (I) which comprise a basic group and an acid group, such as for example guanidino and carboxylic, can be present in the form of Zwiterions (betaines), which are also included in the present invention. The physiologically acceptable $Q^-$ anion which is contained in the compounds of formula (I) when $R_4$ is an alkyl radical substituted by a charged ammonium group, is preferably a monovalent anion or a polyvalent anion equivalent of an organic or inorganic, non-toxic, physiologically and in particular pharmaceutically acceptable acid, for example the anion or an anion equivalent of one of the acids mentioned above which can be used for the formation of the addition salts. $Q^-$ for example can be one of the anions (or anion equivalent) of a group chosen from chlorine, sulphate, phosphate, acetate, trifluoroacetate, citrate, benzoate, maleate, fumarate, tartrate, methanesulphonate and para-toluenesulphonate.

The salts of the compounds of formula (I) can be obtained by standard methods known to a person skilled in the art, for example by combining a compound of formula (I) with an organic or inorganic acid or a base in a solvent or a dispersant or from another salt by cation or anion exchange.

The invention also includes all the salts of the compounds of formula (I) which, because of their low physiological acceptability, cannot be used directly as medicaments, but can be used as intermediate products to implement the subsequent chemical modifications in the compounds of formula (I) or as starting products for the preparation of physiologically acceptable salts.

The present invention also includes all the solvates of the compounds of formula (I) for examples the hydrates, the solvates formed with alcohols, and all the derivatives of the compounds of formula (I), for example the esters, prodrugs and other physiologically acceptable derivatives, as well as the metabolites of the compounds of formula (I).

A more precise subject of the invention is the prodrugs of the compounds of formula (I) which can be converted to compounds of formula (I) in vivo under physiological conditions. The prodrugs of the compounds of formula (I), namely the chemically modified derivatives of the compounds of formula (I), are known to a person skilled in the art in order to obtain the improved properties in a desired fashion.

In order to have more information on the type of prodrug envisaged in the present invention, the following books can be mentioned: Fleicher et al., Advanced Drug Delivery Review 19 (1996) 115–130; Design of prodrugs, H. Bundgaard, Ed., Elsevier, 1985; H. Bungaard, Drugs of the Future 16 (1991) 443;

Saulnier et al. Bioorg. Med. Chem. Lett. 4 (1994) 1985;

Safadi et al. Pharmaceutical Res. 10 (1993) 1350. Among the appropriate prodrugs of the compounds of formula (I) the following can preferably be mentioned:

the prodrugs in the form of esters of the carboxylic groups, in particular of the COOH group, when $R_4$ in $COOR_4$ is a hydrogen atom the prodrugs in the form of acyl and carbamate for the groups containing an acylable nitrogen such as the amino groups and in particular guanidine. In the acylated prodrugs or in the form of carbamate, a hydrogen atom situated on the nitrogen atom is replaced by an acyl group or carbamate, one or more times, for example twice. Among the preferred acyl groups or carbamates, the $R_{10}CO-$, $R_{11}OCO-$ groups, in which $R_{10}$ is a hydrogen or a $(C_1-C_{18})$-alkyl radical, $(C_3-C_{14})$-cycloalkyl, $(C_3-C_{14})$-cycloalkyl-$(C_1-C_8)$-alkyl, $(C_5-C_{14})$-aryl groups, in which 1 to 5 carbon atoms can be replaced by heteroatoms such as N,O,S or $(C_5-C_{14})$-aryl-$(C_1-C_8)$alkyl, in which 1 to 5 carbon atoms in the aryl part can be replaced by heteroatoms such as N,O,S and $R_{11}$ has the same values as $R_{10}$ with the exception of hydrogen can be mentioned.

In the compounds of formula (I), the $R_1$ and $R_2$ radicals preferably represent a hydrogen atom or together form a saturated or unsaturated divalent alkylene radical containing 2 to 5 carbon atoms and in particular 2 to 4 carbon atoms and more particularly 2 or 3 carbon atoms, the alkylene radical of which is non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, said divalent alkylene radical being able to be attached at the level of the carbon-carbon bond to a carbocycle or a heterocycle with 5 to 7 members, containing 1 or 2 nitrogen atoms, saturated or unsaturated, non-substituted or substituted by 1 or 2 $R_3$ radicals.

Among the compounds of formula (I), $R_1$ and $R_2$ preferably represent a hydrogen atom or a $-(CH_2)_p-$ group, in which p is 2, 3, 4 or 5, preferably 2, 3 or 4, more particularly 2 or 3, and which is non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, the said $-(CH_2)_p-$ radical being able to be attached at the level of the carbon-carbon bond to a carbocycle or a heterocycle with 5 to 7 members, containing 1 or 2 nitrogen atoms, saturated or unsaturated, non-substituted or substituted by 1 or 2 $R_3$ radicals.

$R_3$ is preferably an alkyl or alkoxy group containing 1 to 6 carbon atoms or a $CF_3$ group.

$R_4$ is preferably a hydrogen atom or an alkyl group containing 1 to 6 carbon atoms non-substituted or substituted by a group chosen from $(C_1-C_4)$-alkoxy, $(C_1-C_4)$-alkyl-$SO_2$ and $NR_9R_9'$ in which $R_9$ and $R_9'$ independently from one another represent a hydrogen atom or $(C_1-C_4)$-alkyl. $R_4$ is quite particularly a hydrogen atom or an alkyl group containing 1 to 4 carbon atoms non-substituted or substituted by the radicals mentioned above.

$R_5$ is preferably a $CO_2R_6$, $SO_2R_6$, $SO_2NHR_6$ or $SO_2NHCO_2R_6$ group.

$R_6$ is preferably a $(C_1-C_8)$-alkyl or naphthyl radical, non-substituted or substituted by $R_3$, a mono- bi- or tri-cycloalkyl radical containing 3 to 12 carbon atoms or $(C_3-C_{12})$ (mono-, bi- or tri-)-cycloalkyl-$(C_1-C_6)$-alkyl or the radical of formula (II)

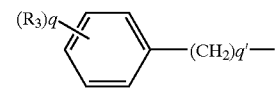

in which the $R_3$ radicals can be identical or different, and can be situated at any position of the phenyl radical, q is equal to 0.1, 2 or 3, preferably 0 or 1 and more particularly 0 and q' is equal to 0 or 1.

$R_6$ more particularly represents an alkyl radical containing 1 to 4 carbon atoms, a phenyl radical mono, bi or trisubstituted by $(C_1-C_6)$-alkyl, a naphthyl radical, an adamantylmethyl radical or the radical of formula (II) in which q is 0 or 1. $R_6$ quite particularly represents the radical of formula (II) with q equal to 0 or 1 and q' equal to 1, that is to say a benzyl radical non-substituted or monosubstituted in ortho, meta or para position by $R_3$.

$R_7$ is preferably a hydrogen atom or an alkyloxycarbonyl group containing 2 to 7 carbon atoms, more particularly hydrogen or alkyloxy-carbonyl containing 2 to 5 carbon atoms and quite particularly hydrogen.

$R_8$ is preferably a hydrogen or halogen atom and more particularly a hydrogen atom.

The preferred compounds of formula (I) are the compounds in which one or more radicals have the preferred meanings.

A particular subject of the invention is a compound of formula (I')

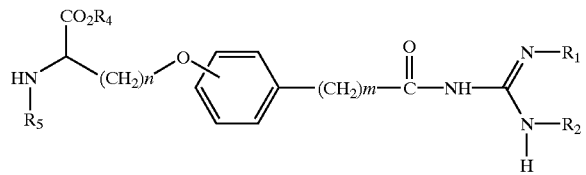

in which $R_1$ and $R_2$ represent a hydrogen atom or together form a saturated or unsaturated divalent alkylene radical containing 2 to 5 carbon atoms or more particularly represent a hydrogen atom or together form a —$(CH_2)_p$— group, in which p is 2, 3, 4 or 5, preferably 2, 3 or 4, more particularly 2 or 3, said alkylene radical or —$(CH_2)_p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$cycloalkyl and $(C_3-C_{12})$-cycloalkyl-$(C_1-C_6)$-alkyl and oxo, said alkylene or —$(CH_2)_p$— group being able to be attached at the level of the carbon-carbon bond to a carbocycle or a heterocycle containing 1 or 2 nitrogen atoms, of 5 to 7 members, saturated or unsaturated, non-substituted or substituted by $R_3$ and in particular by 1 or 2 $R_3$ radicals;

$R_3$ represents an alkyl or alkyloxy group containing 1 to 6 carbon atoms;

$R_4$ represents a hydrogen atom or an alkyl group containing 1 to 6 carbon atoms non-substituted or substituted by a group chosen from $(C_1-C_4)$-alkoxy, $(C_1-C_4)$-alkyl-$SO_2$ and $NR_9R_9'$ in which $R_9$ and $R_9'$ independently from one another represent a hydrogen atom or $(C_1-C_4)$-alkyl, $R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl radical, non-substituted or substituted by $R_3$, a cycloalkyl radical containing 3 to 12 carbon atoms or $(C_3-C_{12})$-cycloalkyl-$(C_1-C_6)$-alkyl or the radical of formula (II)

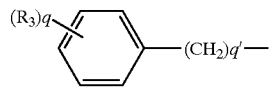

in which the $R_3$ radicals can be identical or different, and can be situated at any position of the phenyl radical, q and q' are equal to 0 or 1;

m is equal to 0, 1, 2 or 3, n is an integer equal to 1, 2 or 3, the said compounds of formula (I') being in all their possible isomer forms, alone or in a mixture in any ratio, the acylguanidine group adjacent to the phenyl being in para or meta position of the oxygen as well as their physiologically acceptable salts and their prodrugs.

A more particular subject of the invention is also a compound of formula (I'), in which $R_1$ and $R_2$ represent a hydrogen atom or together form a saturated or unsaturated divalent alkylene radical containing 2 to 4 carbon atoms or more particularly represent a hydrogen atom or together form a —$(CH_2)_p$— group, in which p is 2, 3 or 4, said alkylene radical or —$(CH_2)_p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, the said alkylene or —$(CH_2)_p$— group being able to be attached at the level of the carbon-carbon bond to a carbocycle or a heterocycle containing 1 or 2 nitrogen atoms, with 5 to 7 members, saturated or unsaturated, non-substituted or substituted by $R_3$ and in particular by 1 or 2 $R_3$ radicals;

$R_3$ represents an alkyl or alkyloxy group containing from 1 to 6 carbon atoms;

$R_4$ represents a hydrogen atom or an alkyl group containing from 1 to 6 carbon atoms;

$R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl radical, non-substituted or substituted by $R_3$, a cycloalkyl radical containing 3 to 12 carbon atoms or $(C_3-C_{12})$-cycloalkyl-$(C_1-C_6)$alkyl or the radical of formula (II)

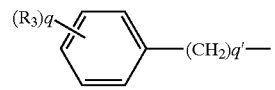

in which the $R_3$ radicals can be identical or different, and can be situated at any position of the phenyl radical, q and and q' are equal to 0 or 1;

m is equal to 0,1, 2 or 3;

n is an integer equal to 1, 2 or 3;

said compounds of formula (I) being in all their possible isomer forms, alone or in a mixture in any ratio, the acylguanidine group adjacent to the phenyl in para or meta position of the oxygen as well as their physiologically acceptable salts and their prodrugs.

A more particular subject of the invention is also a compound of formula (I'), in which $R_1$ and $R_2$ represent a hydrogen atom or together form a saturated or unsaturated divalent alkylene radical containing 2 to 3 carbon atoms or more particularly represent a hydrogen atom or together form a —$(CH_2)_p$— group, in which p is 2 or 3, said alkylene radical or —$(CH_2)_p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, the said alkylene or —$(CH_2)_p$— group being able to be attached at the level of the carbon-carbon bond to a carbocycle or a heterocycle containing 1 or 2 nitrogen atoms, with 5 to 7 members, saturated or unsaturated, non-substituted or substituted by $R_3$ and in particular by 1 or 2 $R_3$ radicals;

$R_3$ represents an alkyl or alkyloxy group containing from 1 to 6 carbon atoms;

$R_4$ represents a hydrogen atom or an alkyl group containing 1 to 6 carbon atoms;

$R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl radical, non-substituted or substituted by $R_3$, a cycloalkyl radical containing 3 to 12 carbon atoms or $(C_3-C_{12})$-cycloalkyl-$(C_1-C_6)$-alkyl or the radical of formula (II)

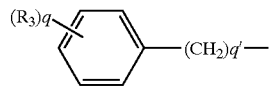

in which the $R_3$ radicals can be identical or different, and can be situated at any position of the phenyl radical, q and q' are equal to 0 or 1;

m is an integer equal to 2;

n is an integer equal to 2;

said compounds of formula (I) being in all their possible isomer forms, alone or in a mixture in any ratio, the acylguanidine group adjacent to the phenyl being in para or meta position of the oxygen as well as their physiologically acceptable salts and their prodrugs.

Among the preferred compounds of formula (I), are the compounds in which the asymmetrical carbon carrying the $CO_2R_4$ and $NHR_5$ groups is of S configuration.

A quite particular subject of the invention is the compounds of formula (I) or (I') as defined above in which $R_5$ is a $CO_2R_6$ radical, $R_6$ being as defined above and in particular —$CH_2Ph$, —$C(CH_3)_3$ and $CH_2$-Adamantyl, said compounds of formula (I) being in all their possible isomer forms, alone or in a mixture in any ratio, the acylguanidine group adjacent to the phenyl being in para or meta position of the oxygen, as well as their physiologically acceptable salts and their prodrugs.

A quite particular subject of the invention is the compounds of formula (I) or (I') as defined above in which $R_5$ is a $SO_2R_6$ radical, $R_6$ being as defined above and in particular an alkyl containing 1 to 6 carbon atoms, naphthyl and phenyl substituted by one or more alkyl radicals containing 1 to 6 carbon atoms or a $CF_3$ group, the said compounds of formula (I) being in all their possible isomer forms, alone or in a mixture in any ratio, the acylguanidine group adjacent to the phenyl being in para or meta position of the oxygen, as well as their physiologically acceptable salts and their prodrugs.

A more particular subject of the invention is the compounds of formula (I) or (I') as defined above in which $R_5$ is an $SO_2NHR_6$ or $SO_2NHCO_2R_6$ radical, $R_6$ being as defined above and in particular —$CH_2Ph$, —$C(CH_3)_3$ and $CH_2$-Adamantyl, the said compounds of formula (I) being in all their possible isomer forms, alone or in a mixture in any ratio, the acylguanidine group adjacent to the phenyl being in para or meta position of the oxygen, as well as their physiologically acceptable salts and their prodrugs.

A subject of the invention is also the compounds of formula (I) the names of which follow:

O—[4-[3-[(aminoiminomethyl)amino]-3-oxopropyl]phenyl]-N-[(phenylmethoxy)carbonyl]-homoserine;

O—[4-[3-oxo-3-[(1,4,5,6-tetrahydro-2-pyrimidinyl)-amino]-propyl]phenyl]-N-[(phenylmethoxy)carbonyl]-homoserine;

ethyl O—[4-[3-oxo-3-[(1,4,5,6-tetrahydro-2-pyrimidinyl)amino]-propyl]phenyl]-N-[(phenylmethoxy)carbonyl]-homoserinate;

ethyl O-[4-[3-oxo-3-[(1,4,5,6-tetrahydro-2-pyrimidinyl)amino]-propyl]phenyl]-N-[(phenylmethoxy)carbonyl]-homoserinate (1-methyl);

O—[4-[3-oxo-3-[(1,4,5,6-tetrahydro-2-pyrimidinyl)amino]-propyl]phenyl]-N-[[(1-tricyclo[3.3.1.1$^{3.7}$]decyl)methoxy]-carbonyl]-homoserine;

O—[4-[3-oxo-3-[(1,4,5,6-tetrahydro-2-pyrimidinyl)amino]-propyl]phenyl]-N-[(2,4,6-trimethylphenyl)sulphonyl]-homoserine O—[4-[3-oxo-3-[(1,4,5,6-tetrahydro-2-pyrimidinyl)amino]-propyl]phenyl]-N-[(1-naphthalenyl)sulphonyl]-homoserine;

O-[3-[3-oxo-3-[(1,4,5,6-tetrahydro-2-pyrimidinyl)amino]-propyl]phenyl]-N-[(phenylmethoxy)carbonyl]-homoserine;

5-[3-[3-oxo-3-[(1,4,5,6-tetrahydro-2-pyrimidinyl)amino]-propyl]phenoxy]-N-[(phenylmethoxy)carbonyl]-norvaline;

A subject of the present invention is also a process for the preparation of the compounds of formula (I). The compounds can generally be prepared, for example during convergent synthesis by coupling two or more fragments which can be derived by retrosynthesis of the compounds of formula (I). In order to avoid the functional groups leading to undesirable or secondary reactions during each stage of synthesis, it can be advantageous or necessary during the synthesis of the compounds of formula (I), to introduce the functional groups in the form of precursors which are subsequently converted to desired functional groups or to temporarily block these functional groups by implementing a protective group strategy suitable for the synthesis which is known to a person skilled in the art (Greene, Wuts protective Group in Organic Synthesis, Wiley 1991).

The compounds of formula (I) can therefore be prepared, for example, by coupling a carboxylic acid or a carboxylic acid derivative of formula (III)

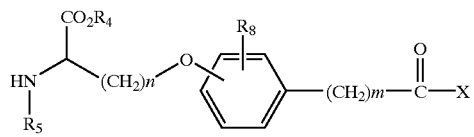

in which $R_4$, $R_5$, n and m are as defined above for formula (I),

X is a parting group which can be substituted by a nucleophile, and where, if appropriate, the functional groups are in the form of precursors or in protected form, with a guanidine or a guanidine derivative of formula (IV)

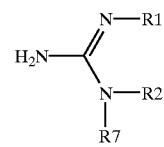

in which $R_1$, $R_2$ and $R_7$ are as defined above in formula (I), and where, if appropriate, the functional groups are in the form of precursors or in protected form, said functional groups optionally present in the form of precursor or in protected form, being subsequently converted into groups present in the compounds of formula (I).

The COX group in formula (III) is preferably the carboxylic acid group or an activated carboxylic acid derivative. X, for example is hydroxyl or halogen, in particular, chlorine or bromine, alkoxy, preferably methoxy or ethoxy, aryloxy, for example phenoxy, pentafluoro-phenyloxy, phenylthio, methylthio, 2-pyridylthio or a nitrogenous heterocycle linked via a hydrogen atom, in particular nitrogen such as 1-imidazolyl for example. X can also be for example $(C_1–C_4)$-alkyl-O—CO—O— or tolylsulphonyloxy and the activated acid derivative can be a mixed anhydride.

If X is a hydroxyl, and therefore if the guanidine of formula (IV) reacts with a carboxylic acid of formula (III), then the carboxylic acid is activated first. The activation can be carried out for example with dicyclohexylcarbodiimide (DCCI) or with O-((cyano(ethoxycarbonyl)-metylene) amino)-1,1,3,3-tetramethyluronium tetrafluoroborate (TOTU; König et al, Proc. 21st Europ. Peptide Symp. 1990 (Eds Giralt, Andreu), Escom, Leiden 1991, p.243) or other activating agents currently used in peptide synthesis.

In addition, the free guanidines of formula (IV), the guanidine salts can also be used in the reaction with the compounds of formula (III), the free guanidines being formed in-situ or in a separate stage by means of a base.

The reaction of an activated carboxylic acid derivative of formula (III) with the guanidine (or derivative) of formula (IV) is preferably carried out in a manner known per se in an organic protic or aprotic, but inert solvent. In this case solvents such as methanol, isopropanol, tert-butanol, dimethylformamide or tetrahydrofuran are used at temperatures ranging from 0° C. to the reflux temperature of these solvents, in particular during the reaction of the methyl or ethyl esters (X is a methoxy or an ethoxy) with the guanidines.

The reactions of the COX type compounds with the free guanidines are advantageously carried out in an inert aprotic solvent such as dimethylformamide, tetrahydrofuran, dimethoxyethane, or dioxane, if appropriate by adding a base such as for example potassium tert-butoxide, sodium methoxide or an organic base such as N-methylmorpholine. However, water can also be used as solvent in the reactions of the compounds of formula (III) with the guanidines of formula (IV), for example by using a base such as sodium hydroxide.

If X is chlorine, the reaction will preferably be carried out by adding an acid trap, for example a base or of an excess of guanidine (or derivative). The reaction mixture is then treated and if desired the reaction product is purified according to the methods known to a person skilled in the art.

The protective groups optionally present in the compounds obtained from the compounds of formula (III) and (IV) are then eliminated by standard methods; for example, the tert-butyl ester groups are converted to carboxylic acid by treatment with trifluoroacetic acid, the benzyl groups are eliminated by hydrogenation or the fluorenylmethoxycarbonyl groups are also eliminated in the presence of secondary amine and other reactions are carried out using standard methods, for example acylation reactions. If necessary, the conversion into physiologically acceptable salts is carried out by methods known to a person skilled in the art.

When $R_5$ represents a hydrogen atom, the functionalization of the amine to a group present in the compounds of formula (I), i.e. in particular when $R_5$ represents a $CO_2R_6$, $SO_2R_6$, $SO_2NHR_6$ or $SO_2NHCO_2R_6$ group is carried out at the level of in the compounds of formulae (III) or (I) and preferably (III). For example in order to obtain the compounds of formula (III) with $R_5=CO_2R_6$ from the corresponding amine a compound of formula X'—$CO_2R_6$ is reacted, X' being a parting group and in particular O-succinic or also a halogen. In order to obtain the compounds of formula (III) with $R_5=SO_2R_6$ from the corresponding amine a compound of formula $R_6SO_2X'$ is reacted, X' being in particular a halogen. In order to obtain the compounds of formula (III) with $R_5=SO_2NHCO_2R_6$ from the corresponding amine a compound of formula X'$SO_2NHCO_2R_6$ is reacted, X' being in particular a halogen, or preferably by the action of an isocyanate of formula $ClSO_2NCO$ in the presence of an $R_6$—OH alcohol. Finally in order to obtain the compounds of formula (III) with $R_5=SO_2NHR_6$ from the corresponding amine a $ClSO_2NCO$ type isocyanate is firstly reacted in the presence of a terbutyl alcohol, then a halide of formula $R_6X$ and finally a deprotection agent of the BOC group.

The starting compounds of formula (III) and (IV) which are then linked in order to produce the compounds of formula (I) are commercially available, and can be prepared according to the methods described in literature or also are accessible by analogy. The preparation of the compounds of formula (III) is illustrated in the diagram described below, it being understood that the present invention is not restricted to these syntheses or these starting products. It is not a major difficulty for a person skilled in the art to envisage modifications to the syntheses described in our Application for the preparation of other compounds of formula (I) according to the invention.

Therefore the compound of formula (V) which is commercially available can be condensed with the compound of formula (VI) (described in Arch. Pharm. (1995) 328, 367) in order to produce a compound of formula (VII). This condensation can be carried out for example in the presence of a base such as potassium carbonate and a halide or any other medium encouraging the nucleophilic substitutions known to a person skilled in the art. The compound of formula (VII) is an example of a compound of formula (III) in which X is methoxy. This condensation can also be carried out directly with the alcohol corresponding to the mesylate of formula (VI) (described in Synthesis (1988),786), (case where m=2) or in Chem. Lett. (1996), 8, 621–622 (case where m=3) in the presence of a betaine by Mitsunobu's reaction

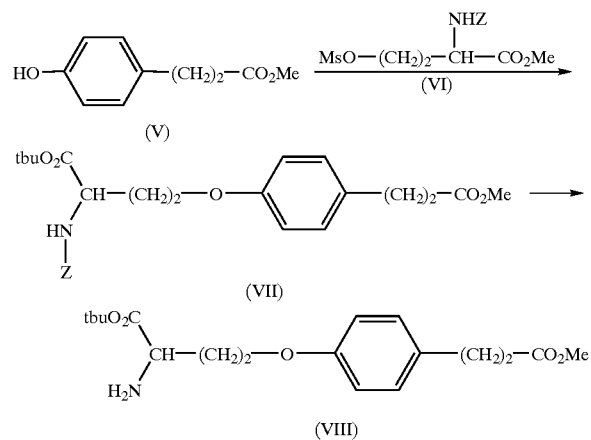

The compounds of formula (I) are compounds having a pharmacological activity and can therefore be used as medicaments in the treatment or the prevention of bone disease, tumorous diseases as well as cardiovascular disorders.

The compounds of formula (I) as well as their physiologically acceptable salts and their prodrugs can be administered to animals, preferably to mammals and in particular to human beings as therapeutic or prophylactic medicaments.

They can be administered as they are or in a mixture with one or more other compounds of formula (I) or also in the form of a pharmaceutical preparation (pharmaceutical composition) which allows enteral or parenteral administration and which contains an effective dose of at least one compound of formula (I) and/or its physiologically acceptable salts and/or its prodrugs as active ingredient as well as current and pharmaceutically inert supports and/or additives.

A subject of the present invention is therefore the compounds of formula (I) and/or their physiologically acceptable salts and/or their prodrugs as medicaments.

A subject of the present invention is also the use of the compounds of formula (I) and/or their physiologically acceptable salts and/or their prodrugs for the preparation of medicaments intended for the prevention or the treatment of the diseases mentioned above or below, for example for the treatment or prevention of bone diseases.

A subject of the present invention is also the pharmaceutical compositions which permit enteral or parenteral administration and which, contain an effective dose of at least one compound of formula (I) and/or its physiologically acceptable salts and/or its prodrugs as active ingredient as well as one or more pharmaceutically inert supports and if appropriate one or more usual additives.

The medicaments can be administered orally, for example in the form of pills, tablets, coated tablets, film-encased, granules, gelatin capsules and soft capsules, solutions, syrups, emulsion, suspension or aerosol mixture.

Administration can however be carried out by rectal route, for example in the form of suppositories or by parenteral route, for example in the form of injectable solutions or infusions, microcapsules or implants, or by percutaneous route, for example in the form of an ointment, solutions, pigments or colorants, or by another route such as in the form of an aerosol or nasal spray.

The pharmaceutical compositions according to the invention are prepared according to methods known per se, organic or inorganic, pharmaceutically inert supports being added to the compounds of formula (I) and/or their physiologically acceptable salts and/or their prodrugs. For the production of pills, tablets, coated tablets and hard gelatin capsules, it is possible for example, to use lactose, corn starch or its derivatives, talc, stearic acid or its salts, etc. Suitable supports for soft gelatin capsules or suppositories are for example fats, waxes, semi-solid or liquid polyols, natural or modified oils etc. Appropriate vehicles for the preparation of solutions, for example injectable solutions, emulsions or syrups are for example water, alcohol, glycerol, polyols, sucrose, inverted sugars, glucose, vegetable oils, etc. Suitable supports for the microcapsules or the implants are for example glyoxilic acid and lactic acid copolymers. The pharmaceutical preparations normally contain 0.5% to 90% by weight of the compounds of formula (I) and/or their physiologically acceptable salts.

In addition to the active ingredients and the supports, the pharmaceutical preparations can contain additives such as for example diluting agents, disintegration agents, binding agents, lubricants, wetting agents, stabilisers, emulsifiers, preservatives, sweetening agents, coloring flavouring or aromatizing agents, thickeners, buffering agents, and solvents or solubilizing agents or agents to obtain a delayed release effect and also salts to modify the osmotic pressure, coating agents or antioxidants.

They can also contain two or several compounds of formula (I) and/or their physiologically acceptable salts and/or their prodrugs. Moreover, in addition to at least one or more compounds of formula (I) and/or their physiologically acceptable salts and/or their prodrugs, they can contain at least one or more other active ingredients which can be used for therapeutic or prophylactic uses.

The pharmaceutical preparations (pharmaceutical compositions) normally contain 0.2 to 500 mg, and preferably 1 to 200 mg of the compound of formula (I) and/or their physiologically acceptable salts and/or their prodrugs.

The compounds of formula (I) are quite particularly antagonists of vitronectin receptors and are therefore capable for example of inhibiting the adhesion of osteoclasts on the surface of the bone and therefore bone resorption by the osteoclasts.

The action of the compounds of formula (I) can be demonstrated for example in a test in which the inhibition of the binding of vitronectin to the cells which contain the vitronectin receptor is determined. Further information about this test is given below. As antagonists of the vitronectin receptor, the compounds of formula (I) and their physiologically acceptable salts and their prodrugs are in general suitable for the treatment or prevention of diseases linked to the interactions between the vitronectin receptors and their ligands, in the process of cell-cell or cell-matrix interaction or which can be influenced by the inhibition of interactions of this type, to relieve or cure when an inhibition of interactions of this type is desired. As explained at the beginning, such an interaction plays an important role in bone resorption, in angiogenesis or in the proliferation of smooth muscle vascular cells.

Bone diseases in which the treatment or prevention require the use of the compounds of formula (I), are in particular osteoporosis, hypercalcemia, osteopenia, for example caused by bony metastases, dental disorders for example parodontitis, hyperparathyroidism, periarticular erosions in rheumatoid arthritis, and Paget's disease. Moreover the compounds of formula (I) can be used to relieve, prevent or treat bone disorders which are caused by treatments, by glucocorticoids, therapies linked to taking steroids or corticosteroids or by male or female sex hormone deficiencies.

All these disorders are characterized by bone loss, which is caused by a lack of equilibrium between bone formation and bone destruction and which can be favourably influenced by the inhibition of bone resorption by the osteoclasts. Besides this use as inhibitor of bone resorption mediated via the osteoclasts, the compounds of formula (I) and their physiologically acceptable salts and their prodrugs are used as inhibitors of tumorous growth or cancerous metastases, in the treatment of inflammatory disorders, for the treatment or prevention of cardiovascular disorders, such as arteriosclerosis or the recurrence of stenosis, or the treatment or prevention of nephropathy or retinopathy such as for example diabetic retinopathy.

The compounds according to the invention can also have an activity vis-à-vis other integrins which interact with their ligand via the tripeptide sequence RGD ($\alpha_v\beta_1$, $\alpha_v\beta_5$, $\alpha_{IIb}\beta_3$), giving them properties which can be used pharmacologically to treat the pathologies associated with these receptors.

This activity vis-à-vis the integrins therefore makes the compounds of formula (I) of use in the prevention or treatment of numerous diseases such as those mentioned above.

When the compounds of formula (I) are used, the doses can vary within wide limits and must be set according to the person treated. This depends for example on the compound used or the nature and severity of the disease to be treated, if the conditions are serious or chronic or if a prophylactic treatment is used.

In the case of administration by oral route, the daily dose in general varies from 0.01 to 100 mg/kg and preferably from 0.1 to 50 mg/kg, in particular from 0.1 to 5 mg/kg. For example for an adult weighing 75 kg a daily dose can be envisaged varying from 0.3 to 0.5 mg/kg.

In the case of administration by intravenous route, the daily dose varies approximately from 0.01 to 100 mg/kg and preferably from 0.05 to 10 mg/kg.

The daily dose can be divided, in particular in the case of the administration of a large quantity of active ingredient, in several, for example 2, 3 or 4 parts. If appropriate, depending on individual behaviour, it may be necessary to administer different increasing or decreasing doses. Apart from the use of the compounds of formula (I) as medicaments, their use as a vehicle or support for active ingredients in order to transport these active ingredients in a specific manner towards a target (Drug targeting, see Targeted Drug Delivery, R C Juliano, Handbook of Experimental Pharmacology, Vol 100, Ed. Born, G. V. R. et al, Springer Verlag). The active ingredients which can be transported are in particular those used for the treatment or prevention of the diseases mentioned above.

The compounds of formula (I) and their salts can also be used as a diagnostic agent, for example for in vitro methods or as an auxiliary in biochemical studies in which blocking the vitronectin receptor or influencing the cell-cell or cell-matrix interactions are desired. They can moreover be used as an intermediate for the preparation of other compounds, in particular other active ingredients, which are accessible from the compounds of formula (I), for example by modification or introduction of radicals or functional groups.

EXAMPLES

The products were identified by mass spectrometry (MS), infrared (IR) and/or NMR spectrometry. The compounds, which were purified by chromatography using a eluent which contains for example acetic or trifluoroacetic acid, and which are then dried or in which during the last stage of synthesis, trifluoroacetic acid for example was used to eliminate a tert-butyl protective group, sometimes containing, depending on the manner in which the product was dried, the acid originating from the eluent or from the last stage of synthesis and therefore is partially or completely in the form of the salt of the acid used, for example in the form of a salt of acetic or trifluoroacetic acid. They can also be more or less hydrated.

Abbreviations/Chemical Names Optionally Used:
PCC: pyridine chlorochromate; DMF: dimethylformamide; THF: tetrahydrofuran; MeOH: methanol; AcOEt: ethyl acetate; TFA: trifluoroacetic acid; TEA: triethylamine; sh. (Shoulder); S (strong); s (singlet); d (doublet); t (triplet); b (broad); m (multiplet).

Preparation P1

Methyl 4-[4-[(1,1-Dimethylethoxy)]-4-oxo-3-[[(phenylmethoxy)-carbonyl]amino]butoxy]-benzenepropanoate

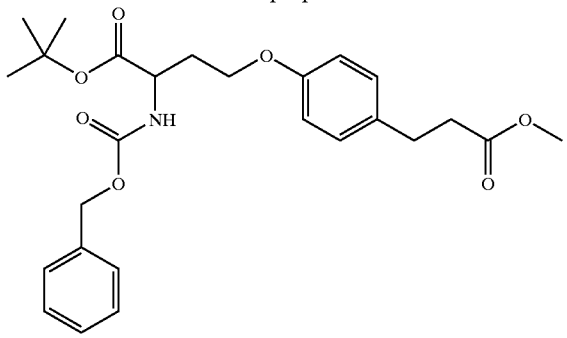

Method 1

500 mg of O-(methyl-sulphonyl) of 1,1-dimethylethyl N-[(phenylmethoxy)carbonyl]-L-homoserinate prepared according to Arch. Pharm. (1995) 328, 367 in 8 ml of THF and 8 ml of DMF is added under argon to a solution of 210 mg of methyl 4-hydroxybenzene propanoate and 330 mg of potassium carbonate in 4 ml of THF and 4ml of DMF, a few crystals of potassium iodide are added and the reaction medium is heated under reflux for approximately two hours. After evaporation under reduced pressure, a white solid is obtained which is purified by chromatography eluting with a AcOEt/Cyclohexane mixture in a 20/80 ratio, then in a $CH_2Cl_2/MeOH/NH_4OH$ mixture in a 99/1/0.5 ratio. 360 mg of expected product is obtained.

IR (CHCl$_3$);
3430 cm$^{-1}$ (NH); 1726 cm$^{-1}$ (C=O); 1612, 1585 and 1513 cm$^{-1}$ (aromatic and amide II).

Method 2

223 mg of betaine ((T-4)-[(3,3-dimethyl)-1,2,5-thiadiazolidine-kappa.N5)1,1-dioxidato (2-)]triphenylphosphorus) prepared according to J. Org. Chem. (1994) 59, 2289 (RN=155632-33-0) is added under argon over 15 minutes to a solution of 100 mg of methyl 4-hydroxybenzene propanoate and 116 mg of 1,1-dimethylethyl N-[(phenylmethoxy)carbonyl]-L-homoserinate in 5 ml of $CH_2Cl_2$ (dichloromethane). The reaction medium is agitated for 30 minutes at ambient temperature then evaporated under reduced pressure. The oil obtained is taken up in 10 ml of $CH_2Cl_2$ and 50 ml of ether, the organic phase is washed, dried then evaporated under reduced pressure in order to obtain 330 mg of crude product which is purified by chromatography eluting with an AcOEt/Cyclohexane 2/8 mixture. On the one hand, 58 mg of pure product and 120 mg of an oil is obtained which is repurified by chromatography eluting with a $CH_2Cl_2/MeOH/NH_4OH$ mixture 99/1/0.5. 75 mg of pure expected product is obtained.

Preparation P2

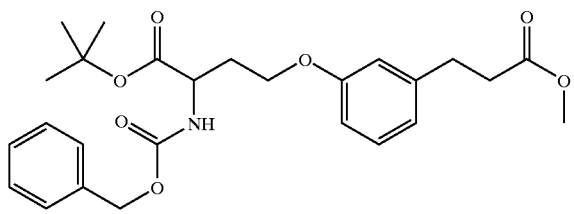

Methyl 3-[4-[(1,1-Dimethylethoxy)]-4-oxo-3-[[(phenylmethoxy)-carbonyl]amino]butoxy]-benzenepropanoate Stage A: Methyl 3-Hydroxy-benzenepropanoate 1 g of 3-hydroxy-benzenepropanoic acid is mixed in 20 ml of methanol and 8 drops of sulphuric acid, the reaction medium is taken to reflux for 2 hours then evaporated under reduced pressure and purified by chromatography eluting with an AcOEt/Cyclohexane mixture 50/50. 1.07 g of expected product is obtained.

IR (CHCl$_3$): 3595 cm$^{-1}$ and associated (OH); 1732 cm$^{-1}$ (C=O of the methyl ester, Me: 1439 cm$^{-1}$); 1614, 1599, 1591, 1491 cm$^{-1}$ Aromatic.

Stage B:

The operation is carried out as in Preparation 1 (Method 2) starting from 270 mg of the phenol prepared in Stage A, 309 mg of 1,1-dimethyl-ethyl N-[(phenylmethoxy)carbonyl]-L-homoserinate and 616 mg of betaine. 320 mg of expected product is obtained.

IR (CHCl$_3$) Absence of OH; 3426 cm$^{-1}$ (NH); 1725 cm$^{-1}$ (C=O) 1602, 1585 and 1507 cm$^{-1}$ (Aromatic+Amide II)

Preparation P3

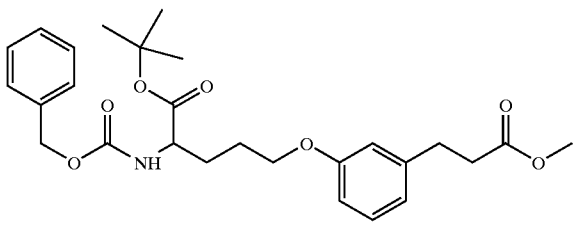

Methyl 3-[5-[(1,1-Dimethylethoxy)]-5 oxo-4-[[(phenylmethoxy)-carbonyl]amino]pentoxy]-benzenepropanoate The operation is carried out as in Preparation 1 (Method 2) starting from 270 mg of the phenol prepared in Stage A of Preparation 2 and 323 mg of 1,1-dimethylethyl 5-hydroxy-N-[(phenylmethoxy)carbonyl]-norvalinate and 616 mg of betaine. 170 mg of expected product is obtained.

IR (CHCl$_3$) Absence of OH 3430 cm$^{-1}$ (NH); 1726 cm$^{-1}$ (C=O) 1602, 1585 and 1508 cm$^{-1}$ (Aromatic+Amide II)

Example 1

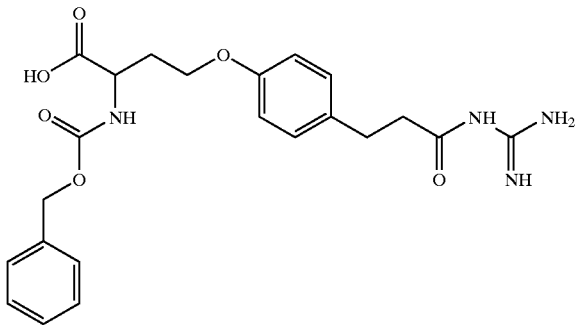

O—[4-[3-[(aminoiminomethyl)amino]-3-oxopropyl]phenyl]-N-[(phenylmethoxy)carbonyl]-homoserine Stage A: (1,1-Dimethyl)ethyl O—[4-[3-[(aminoiminomethyl)amino]-3-oxopropyl]phenyl]-N-[(phenylmethoxy)carbonyl]-homoserinate 40 mg of guanidine base is added to a solution of 100 mg of P1 ester in 2 ml of DMF and the reaction medium is agitated at ambient temperature under argon for 4 hours and evaporated under reduced pressure. 140 mg of a crude product is obtained which is purified by chromatography eluting with a CH$_2$Cl$_2$/MeOH/AcOH/H$_2$O mixture 90/10/1/1 in order to obtain 60 mg of pure expected product.

IR (CHCl$_3$) 3422, 3366 cm$^{-1}$ (NH/NH$_2$); 1717 cm$^{-1}$ (C=O) 1611, 1603, 1554 and 1513 cm$^{-1}$ (Aromatic+C=N+Amide II+NH/NH$_2$)

Stage B: O—[4-[3-[(aminoiminomethyl)amino]-3-oxopropyl]phenyl)]-N-[(phenylmethoxy)carbonyl]-homoserine 3 ml of trifluoroacetic acid (TFA) (3 times 1 ml over 6 hours) at +5° C. is added to a solution of 70 mg of the ester obtained in Stage A in 2 ml of CH$_2$Cl$_2$, the reaction medium is agitated for 7 hours then evaporated under reduced pressure after the addition of toluene. 0.5 ml of methanol and 1 ml of ethyl acetate are then added, and after filtration, the filtrate is poured into 10 ml of isopropyl ether to which 2 ml of pentane is added. After filtration, the solid is dried under reduced pressure and 30 mg of expected product is obtained.

IR nujol: General absorption OH/NH; 1722, 1705 and 1661 cm$^{-1}$ (C=O); 1613, 1569, 1540 and 1512 cm$^{-1}$ (C=N+Aromatic+Amide II+NH/NH$_2$).

NMR (DMSO) 2.00 (m) and 2.16 (m)1CH$_2$; 2.99 (m) and 2.70 (m) 2CH$_2$; 3.97 (t, Ph—O—C$\underline{H}_2$—CH$_2$); 4.06 (m, CO—C$\underline{H}$—NHCO); 5.01 (s, CO$_2$C$\underline{H}_2$Ph); 6.76 and 7.11 (AA'BB', C—Ph—O); 7.15 to 7.40 (m, C—Ph)

Example 2

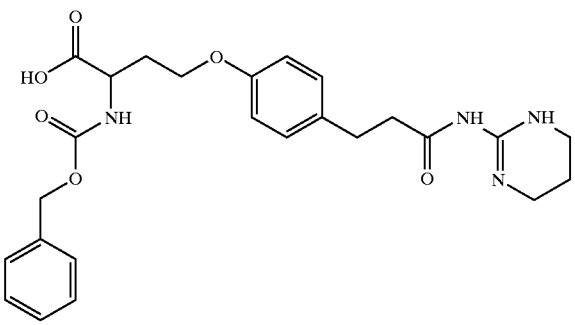

O—[4-[3-oxo-3-[(1,4,5,6-tetrahydro-2-pyrimidinyl)amino]-propyl]phenyl]-N-[(phenylmethoxy)carbonyl]-homoserine Stage A: (1,1-Dimethyl)ethyl O—[4-[3-oxo-3-[(1,4,5,6-tetrahydro-2-pyrimidinyl) amino]-propyl]phenyl]-N-[(phenylmethoxy)carbonyl]-homoserinate 3.52 g of the P1 ester and 1.48 g of amino tetrahydropyrimidine base are mixed together under argon in 35 ml of DMF, followed by agitation for 5 hours at ambient temperature, evaporating under reduced pressure until 5.12 g of crude product is obtained which is purified by chromatography eluting with a CH$_2$Cl$_2$/MeOH/AcOH/H$_2$O mixture 90/10/1/1. 1.79 g of pure expected product is obtained.

IR (CHCl$_3$)

3428, 3264 cm$^{-1}$+general absorption (NH); 1716, 1685 (sh.) and 1672 cm$^{-1}$ (Max) (C=O); 1639 (sh.), 1612, 1577 and 1512 (S) cm$^{-1}$ (C=N+Aromatic+Amide II).

Stage B: O—[4-[3-oxo-3-[(1.4,5,6-tetrahydro-2-pyrimidinyl) amino]-propyl]phenyl]-N-[(phenylmethoxy)carbonyl]-homoserine The operation is carried out as in Example 1 Stage B starting from 900 mg of the ester prepared in the previous stage and 12 ml of TFA in dichloromethane. 750 mg of expected product is obtained.

IR (CHCl$_3$)

3424, 3264 cm-1 (NH), general absorption OH/NH; 1710, 1695 cm$^{-1}$ (C=O); 1670 cm$^{-1}$ (C=O+C=N)1613, 1569 and 1512 cm$^{-1}$ (C=N+Aromatic+Amide II+NH/NH$_2$).

NMR (CDCl$_3$)

1.95 (m) and 2.33 (ml 2 CH$_2$; 2.72 (t) and 2.86 (t) =C—C$\underline{H}_2$—C$\underline{H}_2$ CO; 3.39 (m, 2=N—CH$_2$); 4.05 (m, Ph —O—C$\underline{H}_2$—CH$_2$); 4.47 (m, CO—C$\underline{H}$—NHCO); 5.11 (s, CO$_2$C$\underline{H}_2$Ph); 5.81 (d, =C—N$\underline{H}$—CH); 6.73 and 7.05 (AA'BB', C—Ph—O); 7.34 (s, C—Ph); 10.38 (bs, mobile H)

Example 3

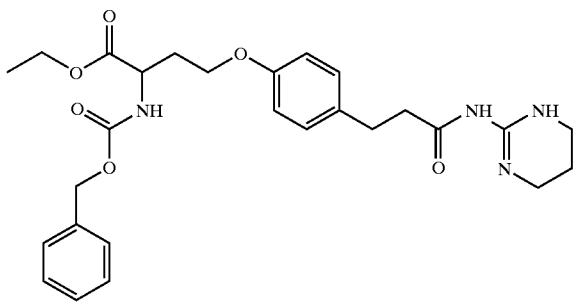

Ethyl O—[4-[3-oxo-3-[(1.4,5,6-tetrahydro-2-pyrimidinyl)amino]-propyl]phenyl]-N[(phenylmethoxy)carbonyl]-homoserinate 1 drop of sulphuric acid is added to 50 mg of the acid prepared in Example 2 in 1 ml of ethanol, the reaction medium is heated at 50° C. for 6 hours then evaporated under reduced pressure until 70 mg of a colourless oil is obtained which is chromatographed eluting with a $CH_2Cl_2$/MeOH/$H_2O$/AcOH mixture 90/10/1/1. 35 mg of pure expected product is obtained.

IR ($CHCl_3$)

3434 cm$^{-1}$+associated (NH); 1718, 1688 and 1666 cm$^{-1}$ (C=O); 1607, 1590 and 1512 cm$^{-1}$ (conjugated system+Aromatic+Amide II).

NMR ($CDCl_3$)

1.25 (t) 4.21 (m) $CO_2Et$; 1.96 (t) 2.31 (m)2 central $CH_2$'s; 2.72 (t, 2H) 2.89 (t,2H) =C—$CH_2$—$CH_2$—C=; 3.39 (m,4H, =C—N—$CH_2$); 4.01 (t, Ph—O—C$\underline{H}_2$—$CH_2$); 4.54 (m, CO—C$\underline{H}$—NHCO); 5.11 (s, $CO_2C\underline{H}_2Ph$); 5.62 (b,broad NHCO); 6.75 and 7.13 (AA'BB', C—Ph—O); 7.35 (m,5H aromatic C—Ph).

Example 4

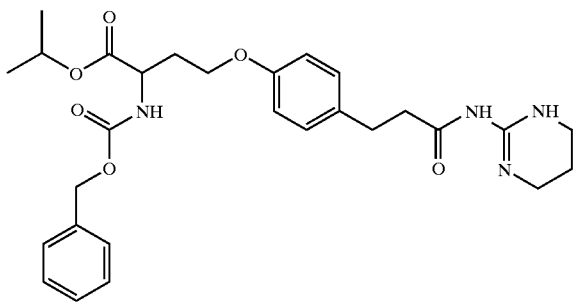

(1-Methyl)ethyl O—[4-[3-oxo-3-[(1.4,5,6-tetrahydro-2-pyrimidinyl)amino]-propyl]phenyl]-N-[(phenylmethoxy) carbonyl]-homoserinate The operation is carried out as in Example 3 but starting from 78 mg of the acid prepared in Example 2 and 5 ml of isopropanol. 50 mg of pure expected product is obtained.

IR ($CHCl_3$)

3424, 3250 cm$^{-1}$ NH absorption; 1717 and 1688 (C=O); 1638, 1608, 1554 and 1512 cm$^{-1}$ (C=O+C=N+Aromatic+Amide II).

NMR ($CDCl_3$)

1.24 (m, ($C\underline{H}_3)_2$CHOCO; 5.07 (m, $(CH_3)_2C\underline{H}OCO$; 2.01 (m) 2.29 (m)2 central $CH_2$'s; 2.76 (m, 2H) 2.90 (m,2H) =C—$CH_2$—$CH_2$—C=; 3.44 (m,4H, =C—N—$CH_2$); 4.01 (t,2H Ph—O—C$\underline{H}_2$—$CH_2$); 4.50 (m, CO—C$\underline{H}$—$CH_2$); 5.11 (s, $CO_2C\underline{H}_2Ph$); 5.59 (d,broad NHCO); 6.76 and 7.12 (AA'BB', C—Ph—O); 7.35 (m,5H aromatic C—Ph).

Example 5

O—[4-[3-oxo-3-[(1.4,5,6-tetrahydro-2-pyrimidinyl)amino]-propyl]phenyl]-N-[[(1-tricyclo[3.3.1.1$^{3,7}$]decyl)-methoxy]-carbonyl]-homoserine Stage A: Methyl 4-[3-(amino)-4[(1,1-dimethylethoxy)]-4-oxobutoxy]-benzenepropanoate The mixture constituted by 0.85 g of P1 ester (Preparation 1), 4.0 g of cyclohexene, 5 ml of THF, 1 ml MeOH and a catalytic quantity of Pd(OH)$_2$/C is heated under reflux for 3 hours, followed by filtering the filtrate is evaporated under reduced pressure until a crude product is obtained which is purified by chromatography eluting with a $CH_2Cl_2$/MeOH mixture 95/5. 520 mg of expected product is obtained.

IR ($CHCl_3$)

3390 cm$^{-1}$ ($NH_2$), 1727 cm$^{-1}$ (C=O), 1612, 1584 and 1513 cm$^{-1}$ (aromatic).

Stage B: Methyl 4-[4-[(1,1-dimethylethoxy)]-4-oxo-3-[[[(1-tricyclo-[3.3.1.1$^{3,7}$]decyl)methoxy]carbonyl]-amino]butoxy]-benzenepropanoate 65 mg of triethylamine is added to a solution of 145 mg of the amine prepared in Stage A in 1 ml of dichloromethane, the reaction medium is cooled down to +5° C. and 176 mg of 1-[[[(tricyclo-[3.3.1.1$^{3,7}$]dec-1-yl)methoxy]carbonyl]oxy]-1H-imidazole is added and agitation is carried out for one hour at this temperature then for 1 hour at ambient temperature. After evaporation under reduced pressure, 330 mg of crude product is obtained which is purified by chromatography eluting with an AcOEt/cyclohexane mixture 20/80. 170 mg of expected product is obtained.

IR ($CHCl_3$)

3424 cm$^{-1}$ (NH), 1724 (broad,F, C=O=); 1612.1512 (S) cm$^{-1}$ (aromatic, amide II); 1369, 1155 (S) cm$^{-1}$ tBu.

Stage C: (1,1-dimethyl)ethyl O—[4-[3-oxo-3-[(1,4,5,6-etrahydro-2-pyrimidinyl)amino]-propyl]phenyl]-N-[[(1-tricyclo[3.3.1.1$^{3,7}$]decyl)-methoxy]-carbonyl]-homoserinate The operation is carried out as in Stage A of Example 2 starting from 35 mg of the ester prepared in the previous stage and 33 mg of 1,4,5,6-tetrahydro-2-pyrimidinamine. 20 mg of expected product is obtained after chromatography with an AcOEt/MeOH mixture 80/20. MH+=597+

Stage D: O—[4-[3-oxo-3-[(1,4,5,6-tetrahydro-2-pyrimidinyl) amino]-propyl]phenyl]-N-[[(1-tricyclo [3.3.1.1$^{3,7}$]decyl)-methoxy]-carbonyl]-homoserine The operation is carried out as in Stage B of Example 1 or 2 starting from 85 mg of the ester prepared in the previous stage and 2 ml of trifluoroacetic acid in 2 ml of $CH_2Cl_2$. 35 mg of expected product is obtained.

IR($CHCl_3$)

3424, 3264 cm$^{-1}$+general absorption (OH/NH); 1694, 1667 cm$^{-1}$ (C=O); 1612, 1571 and 1512 cm$^{-1}$ (C=N+aromatic+amide II)

NMR (DMSO)

1.40 to 2.20 (m) 19H aliphatic chain and central $CH_2$'s; 2.59 (m) 2.77 (m) =C—$CH_2$—$CH_2$—C=; 3.30 (m, =C—N—$CH_2$); 3.55 (s, $CO_2C\underline{H}_2$); 3.97 (m, Ph—O—C$\underline{H}_2$—$CH_2$); 4.05 (m, CO—C$\underline{H}$—NHCO); 6.79 and 7.12 (AA'BB', C—Ph—O); 9.82 (m broad) 12.50 (broad) mobile H's.

Example 6

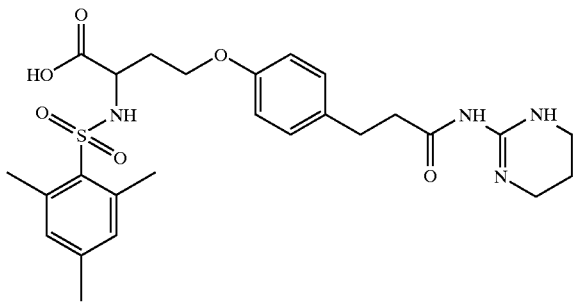

O—[4-[3-oxo-3-[(1.4,5,6-tetrahydro-2-pyrimidinyl) amino]-propyl]phenyl]-N-[(2.4,6-trimethylphenyl) sulphonyl]-homoserine Stage A: Methyl 4-[3-[[(2,4,6 trimethylphenyl)sulphonyl] amino]-4-[(1,1-dimethylethoxy)]-4oxobutoxy] benzenepropanoate.

112 mg of deprotected amine prepared in Stage A of Example 5, 145 g of 2-mesitylenesulphonyl chloride, 58 mg of TEA and 1 ml of THF are agitated for 3 hours at ambient temperature then evaporated under reduced pressure. 290 mg of crude product is obtained which is purified by chromatography eluting with a $CH_2Cl_2$/MeOH mixture 99/1. 145 mg of pure expected product is obtained.

IR ($CHCl_3$)

3340 $cm^{-1}$ (complex NH); 1731 $cm^{-1}$ (C=O); 1605, 1582, 1565 and 1513 $cm^{-1}$ (Aromatic)

Stage B: (1,1-Dimethyl)ethyl O—[4-[3-oxo-3-[(1,4,5,6-tetrahydro-2-pyrimidinyl) amino]-propyl]phenyl]-N-[(2,4, 6-trimethylphenyl)sulphonyl]-homoserinate The operation is carried out as in Stage A of Example 2 starting from 133 mg of the ester obtained in the previous stage and 96 mg of 1,4,5,6-tetrahydro-2-pyrimidinamine in 1 ml of DMF. 80 mg of pure expected product is obtained after chromatography eluting with a MeOH/$CH_2Cl_2$ mixture 95/5.

IR ($CHCl_3$)

3444, 3264 $cm^1$+general absorption (NH); 1728 $cm^{-1}$ (C=O); 1687 and 1662 $cm^{-1}$ (C=O and C=N); 1637, 1605(complex) and 1512 $cm^{-1}$ (conjuguated system+ Aromatic+amide II)

Stage C: O—[4-[3-oxo-3-[(1,4,5,6-tetrahydro-2-pyrimidinyl) amino]-propyl]phenyl]-N-[(2,4,6-trimethylphenyl)sulphonyl]-homoserine The operation is carried out as in Stage B of Example 1 or 2 starting from 70 mg of the ester obtained in the previous stage and 1 ml of TFA in 1.5 of $CH_2Cl_2$. 20 mg of pure expected product is obtained IR (Nujol)

General absorption OH/NH; 1692 $cm^{-1}$ (C=O); 1651 $cm^{-1}$ (C=O+C=N); 1608, 1565 and 1510 $cm^{-1}$ (conjuguated system+aromatic+amide II)

NMR (DMSO)

1.80 to 2.00 central $CH_2$'s; 2.75 (m) 2.50 (masked) =C—$CH_2$—$CH_2$—C=and Ph—Me in ortho position; 2.15 (s, Ph—Me in para position); 3.40 (m, =C—N—$CH_2$); 3.60 to 3.90 (Ph—O—C$\underline{H}_2$—$CH_2$ and CO—C$\underline{H}$—NHCO); 6.65 and 7.12 (AA'BB', C—Ph—O); 6.86 (s,trimethylphenyl); 7.32 (spread) 9.82 mobile H's.

Example 7

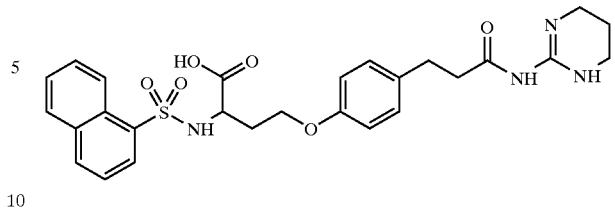

O—[4-[3-oxo-3-[(1.4,5,6-tetrahydro-2-pyrimidinyl) amino]-propyl]phenyl]-N-[(1-naphthalenyl) sulphonyl]-homoserine The operation is carried out as in Example 6 Stages A, B and C but starting from 90 mg of the amine prepared in Stage A of Example 5 and 125 mg of naphthalene-1-sulphonyl chloride.

IR ($CHCl_3$)

3268 $cm^{-1}$+general absorption OH/NH (NH); 1694 $cm^{-1}$ (C=O=; 1667 $cm^{-1}$ (C=O+C=N); conjuguated system+ aromatic+amide II 1612, 1570 and 1513 $cm^{-1}$.

NMR ($CDCl_3$)

1.86 (m, $CH_2$ in position 5'); 3.27 (m, $CH_2$ in position 4' and 6'); 2.04 (m, central $CH_2$ in the chain); 2.56 (t, 2H) 2.75 (t, 2H) Ph—$CH_2CH_2$—CO; 3.67 (m, 1H) 3.83 (m, 2H) $CH_2$OPh and NH—CH—$CH_2$; 6.01 (broad d, NHCH$CH_2$); 6.42 and 6.89 (AA'BB', Ph—O); 7.35 (t, 1H) 7.48 (m, 2H) $H_3$+$H_6$+$H_7$ of the naphthyl; 7.77 (dl) 7.87 (bd) 8.14 (dd) 8.61 (d) $H_2$+$H_4$+$H_5$+$H_8$; 10.32 (m,broad) 13.71 (m, broad mobile 2H's). $MH^+$=539$^+$

Example 8

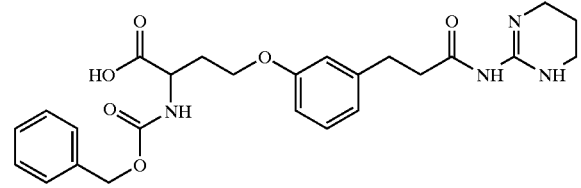

O—[3-[3-oxo-3-[(1,4,5,6-tetrahydro-2-pyrimidinyl) amino]-propyl]phenyl]-N-[(phenylmethoxy) carbonyl]-homoserine;

The operation is carried out as in Example 2 Stages A and B but starting from 300 mg of P2 ester (Preparation 2) and 126 mg of 1,4,5,6-tetrahydro-2-pyrimidinamine in THF. Rf ($CH_2Cl_2$/MeOH/AcOH/$H_2O$ 90/10/1/1)=0.43

IR ($CHCl_3$)

3414, 3264 $cm^{-1}$+General absorption OH/NH (NH); 1754, 1709, 1693 and 1659 $cm^{-1}$ C=O+C=N; 1602, 1574 and 1490 $cm^{-1}$ (aromatic+amide II)

NMR ($CDCl_3$)

1.98 (m) 2.44 (m) central 2$CH_2$'s; 2.18 (m, 1H) 2.96 (m, 3H) =C—$CH_2$—$CH_2$—Ph; 3.41 (t)2×=N—$CH_2$; 4.10 (m) 4.18 (m) Ph—O—C$\underline{H}_2$; 4.34 (q 1H CO—C$\underline{H}$—NH—CO); 5.11 (s, 2H, Ph—$CH_2$—O—CO—); 5.81 (d) and 5.93 (d) 1H=C—$\underline{NH}$—CH; 6.70 (bd, 2H, H4 and H6); 7.01 (bs, 1H) H1; 7.08 (t) H5; 7.36 (m, 5H Ph).

Example 9

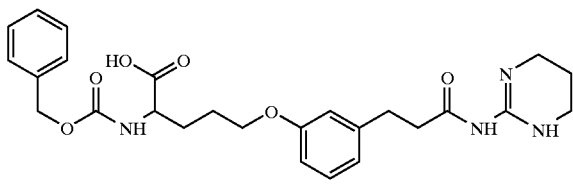

5-[3-[3-oxo-3-[(1.4,5,6-tetrahydro-2-pyrimidinyl) amino]-propyl]phenoxy]-N-[(phenylmethoxy) carbonyl]-norvaline The operation is carried out as in Example 2 Stages A and B but starting from 160 mg of P3 ester (Preparation 3) and 65 mg of 1,4,5,6-tetrahydro-2-pyrimidinamine in THF. Rf ($CH_2Cl_2$/MeOH/AcOH/$H_2O$ 90/10/1/1)=0.45

IR (nujol)

General absorption OH/NH; 1712, 1690 (C=O); 1650, 1575 $cm^{-1}$ (C=O+C=N+aromatic+amide II)

NMR ($CDCl_3$) 1.72 (m,1H) 1.95 (>3H) 2.05 (m, 2H) central $CH_2$'s; 2.76 (m, 1H) 2.95 (m,>3H) =C—$CH_2$—$CH_2$—Ph; 3.36 (m, >4H) =N—$CH_2$; 4.00 to 4.30 (3H, Ph—O—$CH_2$ and CO—C$\underline{H}$—NH —CO); 5.10 (m, 2H, Ph—$CH_2$—O—CO—); 5.78 (bs) 5.90 (d) =C—N$\underline{H}$—CH; 6.67 (d, 1H) 6.75 (d) H4 and H6; 6.92(bs, 1H H2); 7.10(bs, 1H H5); 7.36 (m, Ph); 9.90 (spread mobile H's).

In addition to the compounds specifically exemplified above, other compounds according to the invention are indicated in the table below. These compounds are prepared according to the methods described above or according to variants of them well known to a person skilled in the art. All the variables listed in this table refer to the following generic structure:

| EXAMPLES | R5 | N | m |
|---|---|---|---|
| 10 | $CO_2CH_2Ph$ | 3 | 1 |
| 11 | $CO_2CH_2Ph$ | 2 | 3 |
| 12 | $CO_2CH_2Ph$ | 3 | 2 |
| 13 | $SO_2$—⟨C6H4⟩—tbu | 2 | 2 |
| 14 | $SO_2nPr$ | 2 | 2 |
| 15 | $CO_2CH_2Ph$ | 2 | 1 |
| 16 | $SO_2CH_3$ | 2 | 2 |
| 17 | $SO_2$—⟨C6H4⟩—$CF_3$ | 2 | 2 |

Pharmacological Test

Kistrin/Vitronectin Receptor ($\alpha_v\beta_3$) ELISA Test

Protocol:

96-well MaxiSorp plates are coated overnight at 40 C with 100 µl of Kistrin at 1 µg/ml (dilution in coating buffer: 0.05 M (carbonate)/NaOH pH 9.6. The next day, the wells are emptied and the ligands (kistrin) are then fixed (fixation buffers: PBS containing 0.5% BSA (pH=7.4)) for 1 hour at ambient temperature under gentle agitation of 125 rpm. The wells are washed six times (washing buffer: PBS containing 0.05% Tween 20 (pH 7.7) then the following is added per well and in this order:

- 40 µl of incubation buffer
- 10 µl of the dilution of the product to be tested (the products are diluted in a 50:50 DMSO/water mixture)
- 50 µl of human $\alpha_v\beta_3$ receptor (cf Pytel et al. Methods Enzymol. (1987) 144 (Dilution in incubation buffer, adapted according to the batch of receptor and according to the ligand). The ligand, the $\alpha_v\beta_3$ receptor and the products to be studied are incubated for 3 hours at ambient temperature with gentle agitation of 125 rpm.

The wells are again washed six times, then incubated for 2 hours at ambient temperature with gentle agitation of 125 rpm, in the presence of 100 µl of anti-receptor antibody coupled to a peroxidase (The 4B12-HRP antibody is diluted in incubation buffer (50 mM TRIS pH 7.4; 0.5% BSA; 0.05% Tween 20; 1 mM $MnCl_2$; 50 µM $CaCl_2$; 50 µM $MgCl_2$; 100 mM NaCl). The dilution is to be adapted according to the batch of receptor.

The wells are then washed six times before measurement of the ligand-receptor bond is carried out using a peroxidase developer kit (TBM Microwell Peroxidase Substrate System Kirkegaard; Ref cat 50-76-00).

This kit contains a flask A of substrate (3,3',5,5'-tetramethylebenzidine at 0.4 g/l) and a flask B ($H_2O_2$ to 0.02% in Citrate/Citric acid). Extemporaneously, one volume of A is mixed with one volume of B, then the reaction mixture is distributed at a rate of 100 µl/wells.

The enzymatic reaction develops between 6 to 10 minutes for Kistrin/$\alpha_v\beta_3$ then its development is stopped by the addition of 100 µl of 1 M phosphoric acid. The optical density is determined at 450 nm.

Expression of the Results

The following curve is plotted: the bond percentage as a function of the logarithm of each concentration of the tested product.

For each product IC50 is determined according to the following formula:

IC50=(B0+Bmin)/2
B0=Maximum bond in the absence of any product
Bmin=Minimum bond in the presence of the highest

| EXAMPLE | K/VnR IC50 ($\mu$M) |
|---------|---------------------|
| 1 | 0.031 |
| 2 | 0.0073 |
| 3 | 0.403 |
| 4 | 5 |
| 5 | 0.012 |
| 6 | 0.0033 |
| 7 | 0.0025 |
| 8 | 0.013 |
| 9 | 0.11 |

What is claimed is:

1. A compound selected from the group consisting of a compound of the formula

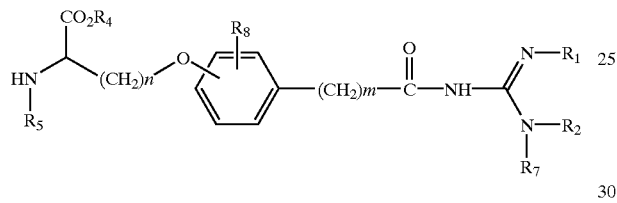

wherein $R_1$ and $R_2$ are independently hydrogen or alkyl of 1 to 6 carbon atoms unsubstituted or substituted by $R_3$, or $R_1$ and $R_2$ together form a divalent alkylene of 2 to 9 carbon atoms, carbon atoms unsubstituted or substituted by $R_3$, or $R_1$ and $R_2$ together form a divalent alkylene of 2 to 9 carbon atoms, saturated or unsaturated, unsubstituted or substituted by at least one member of the group consisting of halogen, $(C_1-C_6)$-alkyl, $C_1-C_6$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl $(C_3-C_{12})$-cycloalkyl-$(C_1-C_6)$-alkyl and oxo, said divalent alkylene being able to be attached at the level of the carbon-carbon bond to a carbocycle or a heterocycle with 5 to 7 members, containing 1 or 2 nitrogen atoms, saturated or unsaturated, unsubstituted or substituted by 1 or 2;

$R_3$ is selected from the group consisting of alkyl of 1 to 8 carbon atoms, alkoxy of 1 to 8 carbon atoms, aryl of 5 to 14 carbon atoms, arylalkyl of 5 to 14 carbon atoms and 1 to 4 alkyl carbon atoms, heteroaryl of 5 to 14 carbon atoms, halogen, $CF_3$, —OH, —$NO_2$, —NH alkyl of 1 to 4 carbon atoms, alkyl

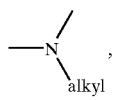

—NH—CO-alkyl and —CO-alkyl is a alkyl of 1 to 4 carbon atoms, $R_4$ is selected from the group consisting of a) hydrogen, b) $(C_1-C_6)$-alkyl-CO—O—$(C_1-C_4)$-alkyl or $(C_1-C_6)$-alkyl group, unsubstituted or substituted by a member selected from the group consisting of hydroxyl, $(C_1-C_4)$-alkoxy, $(C_1-C_4)$-alkyl-$SO_2$, $NR_9R_9'$ and $N^+R_9R_9'R_9''X^-$, in which $R_9$, $R_9'$ and $R_9''$ are independently selected from the group consisting of hydrogen, $(C_1-C_6)$-alkyl, $(C^5-C_{14})$-aryl and $(C_5-C_{14})$-aryl-$C_1-C_6)$-alkyl group and $Q^-$ is a physiologically acceptable anion, c)

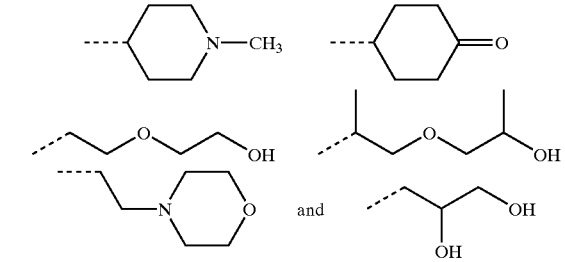

the dotted lines representing the position of the bond; $R_5$ is selected from the group consisting of —$COR_6$, —$CO_2R_6$, —$SO_2R_6$, —$SO_2NHR_6$, —$SO_2NHCOR_6$, —$SO_2NHCO_2R_6$, $CONH_2$ and —$CONHR_6$ in which $R_6$ is selected from the group consisting of $(C_1-C_8)$-alkyl, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$C_1-C_6)$-alkyl, $(C_3-C_{20})$-(mono-, Bi or tri)-cycloalkyl-$(C_1-C_6)$-alkyl, the aryl or heteroaryl being unsubstituted or substituted by 1, to 3, $R_3$;

$R_7$ is selected from the group consisting of hydrogen, $(C_1-C_6)$-alkyl-O—CO—, hydroxyl, $(C_1-C_6)$-alkyl-O—CO—O and nitro;

$R_8$ is selected from the group consisting of hydrogen atom, halogen and alkoxy of 1 to 6 carbon atoms;

m is equal to 0, 1, 2 or 3;

n is an integer equal to 1, 2 or 3;

said compounds of formula (I) being in optical isomeric, enantiomeric and diasteriomeric form, alone or in a mixture in any ratio, the acylguanidine group adjacent to the phenyl being in para or meta position to the oxygen, or its pharmaceutically acceptable salts.

2. A compound of claim 1 of the formula

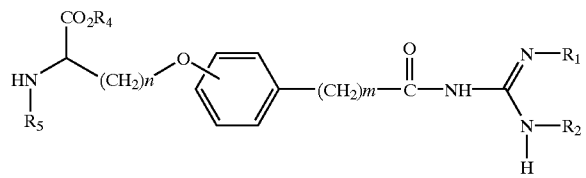

werein $R_1$ and $R_2$ are hydrogen or together form a saturated or unsaturated divalent alkylene of 2 to 5 carbon atoms, said alkylene is unsubstituted or substituted by one or two members of the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $C_5-C_{14})$-heteroaryl, $(C_1-C_6)$-alkyl, $(C_3-C_{12})$-cycloalkyl and $(C_3-C_{12})$-cycloalkyl-$(C_1-C_6)$-alkyl and oxo, said alkylene being able to be attached to the level of the carbon-carbon bond to a carbocycle or a heterocycle containing 1 or 2 nitrogen atoms, with 5 to 7 ring members, saturated or unsaturated, unsubstituted or substituted by 1 to 2;

$R_3$ is alkyl or alkoxy of 1 to 6 carbon atoms;

$R_4$ is hydrogen or alkyl of 1 to 6 carbon atoms unsubstituted or substituted by a member selected from the group ($C_1$–$C_4$)-alkoxy, $C_1$–$C_4$)-alkyl-$SO_2$ and $NR_9R_9'$ in which $R_9$ and $R_9'$ are independently hydrogen or ($C_1$–$C_4$)-alkyl, $R_5$ is selected from the group consisting of hydrogen, —$CO_2R_6$, —$SO_2R_6$, —$SO_2NHR_6$ and —$SO_2NHCO_2R_6$ in which $R_6$ is selected from the group consisting of ($C_1$–$C_8$)-alkyl, naphthyl, unsubstituted or substituted by $R_3$, cycloalkyl radical of 3 to 12 carbon atoms, ($C_3$–$C_{12}$)-cycloalkyl-($C_1$–$C_6$)-alkyl and

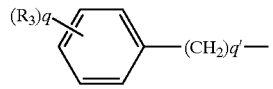

in which the $R_3$ can be identical or different, and can be situated at any position of the phenyl, q and q' are equal to 0 or 1;
m is equal to 0, 1, 2 or 3;
n is an integer equal to 1, 2 or 3, said compounds being in optical isomeric, enantiomeric and diasteriomeric form, alone or in a mixture in any ration, acylguanidine group adjacent to the phenyl being in para or meta position of the oxygen, and their pharmaceutically acceptable salts.

3. A compound of claim 2 wherein $R_1$ and $R_2$ are hydrogen, or together form a saturated or unsaturated divalent alkylene of 2 to 4 carbon atoms, said alkylene being non-substituted or substituted by one or two members of the group consisting of halogen, substituted by one or two members of the group consisting of halogen, ($C_1$–$C_6$)-alkyl, $C_1$–$C_6$)-alkoxy, ($C_6$–$C_{14}$)-aryl, ($C_6$–$C_{14}$)-aryl-$C_1$–$C_6$)-alkyl, ($C_5$–$C_{14}$)-heteroaryl, ($C_5$–$C_{14}$)-heteroaryl-($C_1$–$C_6$)-, ($C_3$–$C_{12}$)-cycloalkyl, ($C_3$–$C_{12}$)-cycloalkyl-($C_1$–$C_6$-alkyl and oxo, said alkylene being able to be attached at the level of the carbon-carbon bond to a carbocycle or a heterocycle containing 1 or 2 nitrogen atoms, with 5 to 7 ring members, saturated or unsaturated, unsubstituted or substituted by 1 or 2 $R_3$;

$R_3$ is alkyl or alkoxy of 1 to 6 carbon atoms;
$R_4$ is hydrogen or alkyl of 1 to 6 carbon atoms;
$R_5$ is selected from the group consisting of hydrogen, —$CO_2$—$R_6$, —$SO_2NHR_6$ and —$SO_2NHCO_2R_6$ in which $R_6$ is selected from the group consisting of ($C_1$–$C_8$)-alkyl, naphthyl, unsubstituted or substituted by $R_3$, cycloalkyl radical of 3 to 12 carbon atoms, ($C_3$–$C_{12}$)-cycloalkyl-($C_1$–$C_6$)-alkyl and

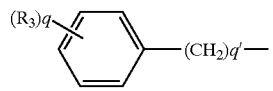

in which the $R_3$ can be identical or different, and can be situated at any position of the phenyl, q and q' are equal to 0 or 1;
m is equal to 0, 1, 2 or 3;
n is an integer equal to 1, 2 or 3;

said compounds being in optical isomeric, enantiomeric and diasteriomeric form, alone or in a mixture in any ratio, the acylguanidine group adjacent to the phenyl being in para or meta position of the oxygen and their pharmaceutically acceptable salts.

4. A compound of formula (I') as defined in claim 2 wherein $R_1$ and $R_2$ are hydrogen, or together form a 2 to 3 saturated or unsaturated divalent alkylene of 2 to 3 carbon atoms, said alkylene being non-substituted or substituted by one or two members of the group consisting of halogen, substituted by one or two members of the group consisting of halogen, ($C_1$–$C_6$)-alkyl, $C_1$–$C_6$)-alkoxy, ($C_6$–$C_{14}$)-aryl, ($C_6$–$C_{14}$)-aryl-$C_1$–$C_6$)-alkyl, ($C_5$–$C_{14}$)-heteroaryl, ($C_5$–$C_{14}$)-heteroaryl-($C_1$–$C_6$)-, ($C_3$–$C_{12}$)-cycloalkyl, ($C_3$–$C_{12}$)-cycloalkyl-($C_1$–$C_6$-alkyl and oxo, said alkylene being able to be attached at the level of the carbon-carbon bond to a carbocycle or a heterocycle containing 1 or 2 nitrogen atoms, with 5 to 7 ring members, saturated or unsaturated, unsubstituted or substituted by 1 or 2 $R_3$;

$R_3$ is alkyl or alkoxy of 1 to 6 carbon atoms;
$R_4$ is hydrogen or alkyl of 1 to 6 carbon atoms;
$R_5$ is selected from the group consisting of hydrogen, —$CO_2R_6$, —$SO_2R_6$, —$SO_2NHR_6$ and —$SO_2NHCO_2R_6$ in which $R_6$ is selected from the group consisting of ($C_1$–$C_8$)-alkyl, naphthyl, unsubstituted or substituted by $R_3$, cycloalkyl radical of 3 to 12 carbon atoms, ($C_3$–$C_{12}$)-cycloalkyl-($C_1$–$C_6$)-alkyl and

II

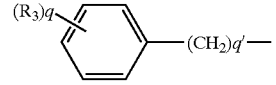

wherein the $R_3$ group can be identical or different, and can be situated at any position of the phenyl, q and q' are equal to 0 or 1;
m is equal to 2;
n is an integer equal to 2, said compounds of formula (I) being in optical isomeric, enantiomeric and diasteriomeric form, alone or in a mixture in any ratio, acylguanidine group adjacent to the phenyl being in para or meta position of the oxygen, and their pharmaceutically acceptable salts.

5. A compound of formula (I) of claim 1 wherein $R_5$ is $CO_2R_6$, $R_6$ being as defined above, said compounds of formula (I) being in optical isomeric, enantiomeric and diasteriomeric form, alone or in a mixture in any ratio, acylguanidine group adjacent to the phenyl being in para or meta position of the oxygen, or its pharmaceutically acceptable salts.

6. A compound of formula (I) of claim 1 wherein $R_5$ is $SO_2R_6$, $R_6$ being as defined in claim 1, said compounds of formula (I) being in optical isomeric, enantiomeric and diasteriomeric form, alone or in a mixture in any ratio, acylguanidine group adjacent to the phenyl being in para or meta position of the oxygen, and their pharmaceutically acceptable salts.

7. A compound of formula (I) of claim 1, wherein $R_5$ is —$SO_2NHR_6$ or —$SO_2NHCO_2R_6$ being as defined in claim 1, said compounds of formula (I) being in optical isomeric, enantiomeric and diasteriomeric form, alone or in a mixture in any ratio, acylguanidine group adjacent to the phenyl being in para or meta position of the oxygen, and their pharmaceutically acceptable salts.

8. A compound of formula (I) of claim 1 selected from the group consisting of

O-[4-[3-((aminoiminomethyl)amino]-3-oxopropyl] phenyl]-N-[(phenylmethoxy)carbonyl]-homoserine;

O-[4-[3-oxo-3-[(1,4,5,6-tetrahydro-2-pyrimidinyl) amino]-propyl]phenyl]-N-[(phenylmethoxy)carbonyl]-homoserine;

ethyl O-[4-[3-oxo-3-[(1,4,5,6-tetrahydro-2-pyrimidinyl) amino]-propyl]phenyl ]-N-[(phenylmethoxy) carbonyl]-homoserinate;

(1-methyl)ethyl O-[4-[3-oxo-3-[(1,4,5,6-tetrahydro-2-pyrimdinyl)amino]-propyl]phenyl]-N-[(phenylmethoxy)carbonyl]-homoserinate;

O-[4-[3-oxo-3-[(1,4,5,6-tetrahydro-2-pyrimidinyl)amino]-propyl]phenyl]-N-[[(1-tricyclo[3.3.1.1$^{3.7}$]decyl)-methoxy]-carbonyl]-homoserine;

O-[4-[3-oxo-3-[(1,4,5,6-tetrahydro-2-pyrimidinyl)amino]-propyl]phenyl]-N-[((2.4,6-trimethylphenyl)sulohonyl]-homoserine;

O-[4-[3-oxo-3-[(1,4,5,6-tetrahydro-2-pyrimidinyl)amino]-propyl]phenyl]-N-[(1-naphthalenyl)sulphonyl]-homoserine;

O-[3-[3-oxo-3-[(1,4,5,6-tetrahydro-2-pyrimidinyl)amino]-propyl]phenyl]-N-[(phenylmethoxy)carbonyl]-homoserine;

5-[3-[3-oxo-3-[(1,4,5,6-tetrahydro-2-pyrimidinyl)amino]propyl]phenoxy]-N-[(phenylmethoxy)carbonyl]-norvaline;

or its pharmaceutically acceptable salts.

9. A process for the preparation of a compound of formula (I) of claim 1 comprising the coupling of at least two fragments which can be derived by retrosynthesis of the compounds of formula (I).

10. The process of claim 9 wherein a carboxylic acid of the formula

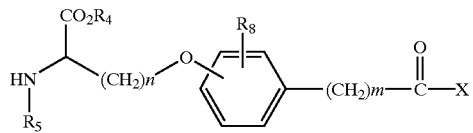

III wherein $R_4$, $R_5$, n and m are as defined in claim 1, X is a leaving group which can be substituted by a nucleophile, and optionally, the functional groups are in the form of a precursor or in protected form, is reacted with a guanidine of the formula

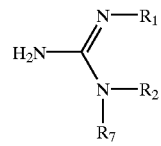

IV wherein $R_1$, $R_2$ and $R_7$ are as defined in claim 1, and optionally, the functional groups are in the form of precursors or in protected form, said functional groups optionally present in the form of precursors or in protected form, being subsequently converted to groups present in the compounds of formula (I).

11. A composition for inhibiting activity on bone resorption or treating osteoporosis comprising an effective amount of a compound of claim 1 and a pharmaceutical carrier.

12. An anti-inflammatory composition comprising an anti-inflammatorily effective amount of a compound of claim 1 and a pharmaceutical carrier.

13. A method of treating osteoporosis in warm-blooded animals comprising administering to warm-blooded animals in need thereof an effective amount of a compound of claim 1 for treating osteoporosis.

14. A method of treating tumors in warm-blooded animals administering to warm-blooded animals in need thereof an antitumorally effective amount of a compound of claim 1.

15. A method of treating cardiovascular disorders in warm-blooded animals comprising administering to 5' warm-blooded animals in need thereof an effective amount of claim 1 to treat cardiovascular disorders.

* * * * *